(12) United States Patent
Draa et al.

(10) Patent No.: US 12,229,833 B1
(45) Date of Patent: Feb. 18, 2025

(54) METHOD, APPARATUS, AND COMPUTER PROGRAM PRODUCT FOR REFORMATTING AN ELECTRONIC PRESCRIPTION TRANSACTION

(71) Applicant: McKesson Corporation, Irving, TX (US)

(72) Inventors: Phillip Draa, Atlanta, GA (US); Jared Burdine, Dunwoody, GA (US)

(73) Assignee: MCKESSON CORPORATION, Irving, TX (US)

(*) Notice: Subject to any disclaimer, the term of this patent is extended or adjusted under 35 U.S.C. 154(b) by 268 days.

(21) Appl. No.: 17/675,616

(22) Filed: Feb. 18, 2022

Related U.S. Application Data

(63) Continuation-in-part of application No. 16/792,413, filed on Feb. 17, 2020, now Pat. No. 11,610,240.

(51) Int. Cl.
  *G06Q 40/08* (2012.01)
  *G06Q 30/00* (2023.01)
  *G06Q 30/0283* (2023.01)

(52) U.S. Cl.
  CPC .......... *G06Q 40/08* (2013.01); *G06Q 30/0283* (2013.01)

(58) Field of Classification Search
  CPC .................. G06Q 40/08; G06Q 30/0283
  See application file for complete search history.

(56) References Cited

U.S. PATENT DOCUMENTS

| 5,012,035 A | 4/1991 | Sartori et al. |
| 5,173,851 A | 12/1992 | Off et al. |
| 5,595,342 A | 1/1997 | McNair et al. |

(Continued)

FOREIGN PATENT DOCUMENTS

| AU | 2003243327 A | 12/2003 |
| CA | 2 482 370 A1 | 3/2006 |

(Continued)

OTHER PUBLICATIONS

M. Bowman and S. Acharya, "Risk Assessment of Pharmacies & Electronic Prescriptions," 2019 IEEE/ACM International Conference on Advances in Social Networks Analysis and Mining (ASONAM), Vancouver, BC, Canada, 2019, pp. 641-644, doi: 10.1145/3341161.3343697. (Year: 2019).*

(Continued)

*Primary Examiner* — Sun M Li
(74) *Attorney, Agent, or Firm* — ALSTON & BIRD LLP

(57) ABSTRACT

A method, apparatus and computer program product are provided for partitioning prescription transaction costs in an electronic prescription transaction by determining a credit amount to be applied to prescription transaction, based on an alternative cash price. In circumstances which an associated prescription claim is rejected or determined to be likely rejected, such as due to a requirement for prior authorization, a patient may still be motivated to purchase a prescription via a cash transaction, particularly with the credit amount applied. The prescription transaction may be reformatted to indicate a cash transaction and include the credit amount, and may exclude benefit information. The credit amount and a reformatted prescription transaction may be transmitted to the pharmacy computer or other third party computer.

8 Claims, 2 Drawing Sheets

(56) References Cited

U.S. PATENT DOCUMENTS

| | | | |
|---|---|---|---|
| 5,628,530 | A | 5/1997 | Thornton |
| 5,726,092 | A | 3/1998 | Mathews et al. |
| 5,757,898 | A | 5/1998 | Nishikawa |
| 5,769,228 | A | 6/1998 | Wroblewski |
| 6,012,035 | A | 1/2000 | Freeman et al. |
| 6,111,218 | A | 8/2000 | Akers et al. |
| 6,463,462 | B1 | 10/2002 | Smith et al. |
| 6,595,342 | B1 | 7/2003 | Maritzen et al. |
| 6,726,092 | B2 | 4/2004 | Goldberg et al. |
| 6,757,898 | B1 | 6/2004 | Ilsen et al. |
| 6,769,228 | B1 | 8/2004 | Mahar |
| 7,155,397 | B2 | 12/2006 | Alexander et al. |
| 7,192,741 | B2 | 3/2007 | Otte et al. |
| 7,337,129 | B1 | 2/2008 | Lowry et al. |
| 7,346,768 | B2 | 3/2008 | DiRienzo |
| 7,409,632 | B1 | 8/2008 | DiRienzo |
| 7,426,476 | B2 | 9/2008 | Munoz et al. |
| 7,734,483 | B1 | 6/2010 | Smith et al. |
| 7,783,383 | B2 | 8/2010 | Eliuk et al. |
| 7,840,424 | B2 | 11/2010 | Wiley et al. |
| 7,856,364 | B1 | 12/2010 | Wiley et al. |
| 7,912,741 | B1 | 3/2011 | Pinsonneault |
| 7,921,021 | B1 | 4/2011 | Newman |
| 8,036,913 | B1 * | 10/2011 | Pinsonneault .......... G06Q 10/10 705/2 |
| 8,036,914 | B1 | 10/2011 | Pinsonneault |
| 8,036,918 | B1 | 10/2011 | Pinsonneault |
| 8,050,943 | B1 | 11/2011 | Wiley et al. |
| 8,060,379 | B1 | 11/2011 | Pinsonneault et al. |
| 8,126,743 | B1 | 2/2012 | Wilk |
| 8,326,773 | B1 | 12/2012 | Bellamy |
| 8,412,537 | B1 | 4/2013 | Fenton et al. |
| 8,442,847 | B1 | 5/2013 | Shrivastava |
| 8,489,415 | B1 | 7/2013 | Ringold |
| 8,521,557 | B1 | 8/2013 | Ringold et al. |
| 8,560,340 | B1 | 10/2013 | Ringold |
| 8,645,162 | B2 | 2/2014 | Boerger et al. |
| 8,671,018 | B2 | 3/2014 | Thomas et al. |
| 8,712,797 | B1 | 4/2014 | Bezdek et al. |
| 8,738,399 | B1 | 5/2014 | Abou Nader et al. |
| 8,786,650 | B1 | 7/2014 | Eller et al. |
| 8,799,018 | B1 | 8/2014 | Rea et al. |
| 8,984,059 | B2 | 3/2015 | Johnson |
| 9,026,507 | B2 | 5/2015 | Shraim et al. |
| 9,100,793 | B2 | 8/2015 | Johnson |
| 9,171,322 | B2 | 10/2015 | Spievak et al. |
| 9,356,947 | B2 | 5/2016 | Shraim et al. |
| 9,760,871 | B1 | 9/2017 | Pourfallah et al. |
| 9,786,023 | B2 | 10/2017 | Cohan et al. |
| 10,109,027 | B1 | 10/2018 | Stack |
| 10,157,262 | B1 | 12/2018 | Pinsonneault |
| 10,331,855 | B1 | 6/2019 | Bratton et al. |
| 10,417,380 | B1 | 9/2019 | Kaye et al. |
| 10,489,552 | B2 | 11/2019 | Pinsonneault |
| 10,496,793 | B1 | 12/2019 | Lawrence et al. |
| 10,565,656 | B1 | 2/2020 | Pinsonneault et al. |
| 10,606,984 | B1 | 3/2020 | Kaye et al. |
| 10,616,146 | B1 | 4/2020 | Hopkins et al. |
| 10,628,797 | B2 | 4/2020 | Shraim et al. |
| 10,642,812 | B1 | 5/2020 | Hopkins et al. |
| 10,713,694 | B1 * | 7/2020 | Harris .................... G06Q 50/22 |
| 10,747,848 | B2 | 8/2020 | Guinan |
| 10,778,618 | B2 | 9/2020 | Karnin et al. |
| 10,862,832 | B1 | 12/2020 | Harris |
| 10,924,545 | B2 | 2/2021 | Momchilov et al. |
| 10,924,585 | B1 | 2/2021 | Harris et al. |
| 10,929,932 | B1 | 2/2021 | Golden et al. |
| 10,978,198 | B1 | 4/2021 | Pinsonneault |
| 10,999,224 | B1 | 5/2021 | Frechen et al. |
| 11,043,293 | B1 | 6/2021 | Salzbrenner |
| 11,443,835 | B1 | 9/2022 | Gangaikondan-Iyer et al. |
| 11,508,471 | B1 | 11/2022 | Anselmi et al. |
| 11,610,240 | B1 * | 3/2023 | Burdine ................. G16H 40/20 |
| 11,636,548 | B1 * | 4/2023 | Hopkins ................ G06Q 10/10 705/4 |
| 2001/0029483 | A1 | 10/2001 | Schultz et al. |
| 2001/0037216 | A1 | 11/2001 | Oscar et al. |
| 2001/0039589 | A1 | 11/2001 | Aho et al. |
| 2001/0056359 | A1 | 12/2001 | Abreu |
| 2002/0002495 | A1 | 1/2002 | Ullman |
| 2002/0004812 | A1 | 1/2002 | Motoyama |
| 2002/0032582 | A1 | 3/2002 | Feeney et al. |
| 2002/0032583 | A1 | 3/2002 | Joao |
| 2002/0035484 | A1 | 3/2002 | McCormick |
| 2002/0087583 | A1 | 7/2002 | Morgan et al. |
| 2002/0111832 | A1 | 8/2002 | Judge |
| 2002/0133379 | A1 | 9/2002 | Lewis et al. |
| 2002/0143579 | A1 | 10/2002 | Docherty et al. |
| 2002/0147614 | A1 | 10/2002 | Doerr et al. |
| 2002/0188552 | A1 | 12/2002 | Kavounas et al. |
| 2002/0198831 | A1 | 12/2002 | Patricelli et al. |
| 2003/0009367 | A1 | 1/2003 | Morrison |
| 2003/0050796 | A1 | 3/2003 | Baldwin |
| 2003/0050799 | A1 | 3/2003 | Jay et al. |
| 2003/0069760 | A1 | 4/2003 | Gelber |
| 2003/0074234 | A1 | 4/2003 | Stasny |
| 2003/0097310 | A1 | 5/2003 | Ono et al. |
| 2003/0130875 | A1 | 7/2003 | Hawash et al. |
| 2003/0149625 | A1 | 8/2003 | Leonardi et al. |
| 2003/0154163 | A1 | 8/2003 | Phillips et al. |
| 2003/0172008 | A1 | 9/2003 | Hage et al. |
| 2003/0187690 | A1 | 10/2003 | Miller |
| 2003/0229540 | A1 | 12/2003 | Algiene |
| 2003/0236747 | A1 | 12/2003 | Sager |
| 2004/0006490 | A1 | 1/2004 | Gingrich et al. |
| 2004/0039599 | A1 | 2/2004 | Fralic |
| 2004/0054685 | A1 | 3/2004 | Rahn et al. |
| 2004/0059607 | A1 | 3/2004 | Ball et al. |
| 2004/0073456 | A1 | 4/2004 | Gottlieb et al. |
| 2004/0073457 | A1 | 4/2004 | Kalies |
| 2004/0078222 | A1 | 4/2004 | Khan et al. |
| 2004/0078234 | A1 | 4/2004 | Tallal, Jr. |
| 2004/0088187 | A1 | 5/2004 | Chudy et al. |
| 2004/0103062 | A1 | 5/2004 | Wood et al. |
| 2004/0117323 | A1 | 6/2004 | Mindala |
| 2004/0148198 | A1 | 7/2004 | Kalies |
| 2004/0153336 | A1 | 8/2004 | Virdee et al. |
| 2004/0199545 | A1 | 10/2004 | Wagner et al. |
| 2004/0236630 | A1 | 11/2004 | Kost et al. |
| 2004/0249745 | A1 | 12/2004 | Baaren |
| 2005/0015280 | A1 | 1/2005 | Gabel et al. |
| 2005/0060201 | A1 | 3/2005 | Connely, III et al. |
| 2005/0065821 | A1 | 3/2005 | Kalies, Jr. |
| 2005/0075932 | A1 | 4/2005 | Mankoff |
| 2005/0080692 | A1 | 4/2005 | Padam et al. |
| 2005/0102169 | A1 | 5/2005 | Wilson |
| 2005/0154627 | A1 | 7/2005 | Zuzek et al. |
| 2005/0187793 | A1 | 8/2005 | Myles |
| 2005/0197862 | A1 | 9/2005 | Paterson et al. |
| 2005/0240442 | A1 * | 10/2005 | Lapsker ................ G06Q 30/02 705/2 |
| 2005/0240473 | A1 | 10/2005 | Ayers, Jr. et al. |
| 2005/0261939 | A1 | 11/2005 | Augspurger et al. |
| 2005/0288972 | A1 | 12/2005 | Marvin et al. |
| 2006/0020514 | A1 | 1/2006 | Yered |
| 2006/0026041 | A1 | 2/2006 | Ullman |
| 2006/0036470 | A1 * | 2/2006 | Oaks ..................... G16H 20/10 705/2 |
| 2006/0085231 | A1 | 4/2006 | Brofman |
| 2006/0085385 | A1 | 4/2006 | Foster et al. |
| 2006/0113376 | A1 | 6/2006 | Reed et al. |
| 2006/0149595 | A1 | 7/2006 | Williams et al. |
| 2006/0149784 | A1 | 7/2006 | Tholl et al. |
| 2006/0184391 | A1 | 8/2006 | Barre et al. |
| 2006/0212318 | A1 | 9/2006 | Dooley |
| 2006/0212345 | A1 | 9/2006 | Soza et al. |
| 2006/0224414 | A1 | 10/2006 | Astrup et al. |
| 2006/0224417 | A1 | 10/2006 | Werner |
| 2006/0224443 | A1 | 10/2006 | Soza et al. |
| 2006/0235747 | A1 | 10/2006 | Hammond et al. |
| 2006/0259363 | A1 | 11/2006 | Jhetam et al. |
| 2007/0005402 | A1 | 1/2007 | Kennedy et al. |
| 2007/0033137 | A1 | 2/2007 | Provost et al. |
| 2007/0043589 | A1 | 2/2007 | Warren et al. |

(56) References Cited

U.S. PATENT DOCUMENTS

| | | |
|---|---|---|
| 2007/0043595 A1 | 2/2007 | Pederson |
| 2007/0050209 A1 | 3/2007 | Yered |
| 2007/0050210 A1* | 3/2007 | Wiley, II .............. G06Q 30/06 |
| | | 705/2 |
| 2007/0067186 A1 | 3/2007 | Brenner et al. |
| 2007/0094133 A1 | 4/2007 | Anandarao et al. |
| 2007/0108053 A1 | 5/2007 | Cramer et al. |
| 2007/0136100 A1 | 6/2007 | Daugherty et al. |
| 2007/0162303 A1 | 7/2007 | Wiley et al. |
| 2007/0168228 A1 | 7/2007 | Lawless |
| 2007/0185799 A1 | 8/2007 | Harrison et al. |
| 2007/0191985 A1 | 8/2007 | Bain |
| 2007/0194352 A1 | 8/2007 | Han |
| 2007/0202886 A1 | 8/2007 | Dhebri et al. |
| 2007/0204043 A1 | 8/2007 | Espinosa et al. |
| 2007/0219813 A1 | 9/2007 | Moore |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0250341 A1 | 10/2007 | Howe et al. |
| 2007/0260750 A1 | 11/2007 | Feied et al. |
| 2007/0276697 A1 | 11/2007 | Wiley et al. |
| 2007/0294765 A1 | 12/2007 | Rihn et al. |
| 2007/0299915 A1 | 12/2007 | Shraim et al. |
| 2008/0033750 A1 | 2/2008 | Swiss et al. |
| 2008/0103836 A1 | 5/2008 | Park et al. |
| 2008/0112411 A1 | 5/2008 | Stafford et al. |
| 2008/0152107 A1 | 6/2008 | Mendiola |
| 2008/0183492 A1 | 7/2008 | Warren et al. |
| 2008/0215361 A1 | 9/2008 | Nunnari et al. |
| 2008/0262948 A1 | 10/2008 | Grady et al. |
| 2009/0006141 A1 | 1/2009 | Karr |
| 2009/0030719 A1 | 1/2009 | Nadas et al. |
| 2009/0064330 A1 | 3/2009 | Shraim et al. |
| 2009/0083064 A1 | 3/2009 | Mahinda |
| 2009/0094051 A1 | 4/2009 | Ard et al. |
| 2009/0100099 A1 | 4/2009 | Buckwalter |
| 2009/0106313 A1 | 4/2009 | Boldyga |
| 2009/0112707 A1 | 4/2009 | Weiss et al. |
| 2009/0198510 A1 | 8/2009 | Ditto |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1 | 6/2010 | Mayaud |
| 2010/0217622 A1 | 8/2010 | Brown et al. |
| 2010/0285821 A1 | 11/2010 | Smeeding et al. |
| 2010/0287001 A1 | 11/2010 | Pearce et al. |
| 2010/0293236 A1 | 11/2010 | Wisner et al. |
| 2011/0015978 A1 | 1/2011 | Welch, Jr. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2011/0288925 A1 | 11/2011 | Thomas et al. |
| 2012/0053958 A1 | 3/2012 | Marshall et al. |
| 2012/0136809 A1 | 5/2012 | Cannata et al. |
| 2012/0143627 A1 | 6/2012 | Ruben et al. |
| 2012/0166268 A1 | 6/2012 | Griffiths |
| 2012/0179481 A1 | 7/2012 | Patel et al. |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1* | 10/2012 | John ...................... G16H 40/67 |
| | | 705/2 |
| 2012/0265591 A1 | 10/2012 | Hwang |
| 2012/0323608 A1 | 12/2012 | Herzlinger |
| 2013/0041968 A1 | 2/2013 | Cohen et al. |
| 2013/0046610 A1 | 2/2013 | Abraham |
| 2013/0103602 A1 | 4/2013 | Melnick et al. |
| 2013/0144715 A1 | 6/2013 | Kranzley et al. |
| 2013/0179180 A1 | 7/2013 | Patra |
| 2013/0197980 A1 | 8/2013 | Lerner et al. |
| 2013/0246082 A1 | 9/2013 | Brylawski et al. |
| 2013/0311389 A1 | 11/2013 | Kaehler et al. |
| 2014/0039911 A1 | 2/2014 | Iyer |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278448 A1 | 9/2014 | Sadeghi et al. |
| 2014/0278456 A1 | 9/2014 | Milosevich et al. |
| 2014/0278531 A1 | 9/2014 | Gupta |
| 2015/0032465 A1 | 1/2015 | Sundar et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1 | 8/2015 | Pinsonneault |
| 2015/0235177 A1 | 8/2015 | Shraim et al. |
| 2015/0269695 A1 | 9/2015 | Pinsonneault et al. |
| 2015/0332422 A1 | 11/2015 | Gilmartin |
| 2015/0371000 A1 | 12/2015 | Pinsonneault |
| 2016/0012465 A1 | 1/2016 | Sharp |
| 2016/0103978 A1 | 4/2016 | Stong |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0321406 A1 | 11/2016 | Timmerman et al. |
| 2016/0321410 A1 | 11/2016 | Timmerman et al. |
| 2016/0358142 A1 | 12/2016 | Hillen |
| 2016/0359795 A1 | 12/2016 | Fehling |
| 2017/0034087 A1 | 2/2017 | Borenstein et al. |
| 2017/0220768 A1 | 8/2017 | Tanner, Jr. et al. |
| 2017/0323295 A1 | 11/2017 | Kranzley et al. |
| 2017/0324695 A1 | 11/2017 | Fischer et al. |
| 2017/0329922 A1 | 11/2017 | Eberting et al. |
| 2018/0012244 A1 | 1/2018 | Leonardi |
| 2018/0366810 A1 | 12/2018 | Nero et al. |
| 2019/0095582 A1 | 3/2019 | Waits |
| 2019/0213212 A1 | 7/2019 | Adato et al. |
| 2019/0252049 A1 | 8/2019 | Fotsch et al. |
| 2019/0385733 A1 | 12/2019 | Kaye et al. |
| 2019/0385734 A1 | 12/2019 | Pinsonneault |
| 2020/0105392 A1 | 4/2020 | Karkazis et al. |
| 2020/0372988 A1 | 11/2020 | Bezdek et al. |
| 2021/0319887 A1 | 10/2021 | Derrick, Jr. et al. |
| 2021/0374876 A1 | 12/2021 | Cedergreen |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 A1 | 5/1991 |
| WO | WO 1995/003569 A2 | 2/1995 |
| WO | WO 1997/025682 A1 | 7/1997 |
| WO | WO 1998/050871 A1 | 11/1998 |
| WO | WO 2000/039737 A1 | 7/2000 |
| WO | WO 2003/098401 A2 | 11/2003 |
| WO | WO 2007/025295 A2 | 3/2007 |
| WO | WO 2007/094772 A1 | 8/2007 |
| WO | WO 2008/092109 A2 | 7/2008 |

(56) References Cited

FOREIGN PATENT DOCUMENTS

OTHER PUBLICATIONS

C. Gemmil, M. (2008). The price elasticity of demand for prescription drugs: An exploration of demand in different settings (Order No. U615895). Available from ProQuest Dissertations and Theses Professional. (1625984575). (Year: 2008) (Year: 2008) (Year: 2008).*
S. Liu, J. C. Xu, G. Liu, H. Xue, D. Bishai and Y. Wang, "Evaluating Cost-Effectiveness of Treatment Options for Diabetes Patients Using System Dynamics Modeling," 2018 Winter Simulation Conference (WSC), Gothenburg, Sweden, 2018, pp. 2577-2588, doi: 10.1109/WSC.2018.8632264. (Year: 2018).*
Zhu VJ, Belsito A, Tu W, Overhage JM. Data for drugs available through low-cost prescription drug programs are available through pharmacy benefit manager and claims data. BMC Clin Pharmacol. Jun. 22, 2012;12:12. doi: 10.1186/1472-6904-12-12. PMID: 22726249; PMCID: PMC3416643. (Year: 2012) (Year: 2012).*
United States Patent and Trademark Office, Non-Final Office Action received for U.S. Appl. No. 17/705,919, dated Aug. 17, 2023, 68 pages, US.
United States Patent and Trademark Office, Final Office Action received for U.S. Appl. No. 17/012,565, dated Jul. 25, 2022, 43 pages, U.S.
United States Patent and Trademark Office, Non-Final Office Action received for U.S. Appl. No. 16/867,286, dated Mar. 31, 2023, 16 pages, US.
United States Patent and Trademark Office, Non-Final Office Action received for U.S. Appl. No. 17/175,939, dated Apr. 26, 2023, 24 pages, US.
United States Patent and Trademark Office, Final Office Action received for U.S. Appl. No. 17/674,366, dated Dec. 15, 2023, 53 pages, US.
United States Patent and Trademark Office, Final Office Action received for U.S. Appl. No. 17/144,426, dated Dec. 19, 2023, 22 pages, US.
United States Patent and Trademark Office, Final Office Action received for U.S. Appl. No. 17/158,118, dated Dec. 19, 2023, 22 pages, US.
United States Patent and Trademark Office, Non-Final Office Action received for U.S. Appl. No. 16/816,460, dated Dec. 22, 2023, 46 pages, US.
U.S. Appl. No. 16/816,460, "Adaptive System and Method for Adjudicating Claims to Reduce Member Responsibility", Unpublished (Filing Date Mar. 12, 2020), (Michael Rea, Inventor), (RC Savings, LLC, Assignee).
United States Patent and Trademark Office, Non-Final Office Action received for U.S. Appl. No. 16/816,460, dated Mar. 3, 2023, 14 pages, U.S.
United States Patent and Trademark Office, Final Office Action received for U.S. Appl. No. 17/162,461, dated May 19, 2023, 23 pages, U.S.
United States Patent and Trademark Office, Advisory Action received for U.S. Appl. No. 17/158,118, dated May 26, 2023, 5 pages, U.S.
United States Patent and Trademark Office, Non-Final Office Action received for U.S. Appl. No. 17/674,366, dated Jun. 6, 2023, 75 pages, U.S.
United States Patent and Trademark Office, Miscellaneous Office Action, Restarting Period, received for U.S. Appl. No. 17/175,939, dated Jun. 14, 2023, 23 pages, U.S.
Viswanthan, Meera, et al., "Interventions to Improve Adherence to Self-administered Medications for Chronic Diseases in the United States," Annals of Internal Medicine, Dec. 4, 2012, retrieved from the Internet at <https://www.acpjournals.org/doi/full/10.7326/0003-4819-157-11-201212040-00538?rfr_dat=cr_pub++0pubmed&url_ver=Z39.88-2003&rfr_id=ori%3Arid%3Acrossref.org> on Jun. 14, 2023, 25 pages.
Dubois, Robert W., "Rx Drug Costs: List Prices Versus Net Prices And The Importance Of Staying Within The Data", Health Affairs Blog, Mar. 2019, 7 pages.
Kamal, Rabah, et al., "What are the recent and forecasted trends in prescription drug spending?" Peterson-KFF Health System Tracker, Feb. 20, 2019, 19 pages, Peterson Center on Healthcare.
Cepeda, Maria Soledad, et al., "Quantification of missing prescriptions in commercial claims databases : results of a cohort study.", Pharmacoepidemiology and Drug Safety, Apr. 2017, pp. 386-392, vol. 26, Epub Jan. 25, 2017 on Wiley Online Library.
United States Patent and Trademark Office, Final Office Action received for U.S. Appl. No. 16/867,286, dated Sep. 8, 2022, 19 pages, U.S.
United States Patent and Trademark Office, Notice of Allowance received for U.S. Appl. No. 16/792,413, dated Sep. 8, 2022, 18 pages, U.S.
United States Patent and Trademark Office, Notice of Allowance received for U.S. Appl. No. 17/012,565, dated Sep. 21, 2022, 11 pages, U.S.
United States Patent and Trademark Office, Notice of Allowance received for U.S. Appl. No. 16/453,509, dated Oct. 3, 2022, 23 pages, U.S.
United States Patent and Trademark Office, Final Office Action received for U.S. Appl. No. 17/175,939, dated Oct. 5, 2022, 30 pages, U.S.
United States Patent and Trademark Office, Nonfinal Office Action received for U.S. Appl. No. 17/162,461, dated Oct. 5, 2022, 47 pages, U.S.
United States Patent and Trademark Office, Nonfinal Office Action received for U.S. Appl. No. 17/158,118, dated Oct. 7, 2022, 46 pages, U.S.
United States Patent and Trademark Office, Final Office Action received for U.S. Appl. No. 16/867,286, dated Sep. 19, 2023, 16 pages, US.
United States Patent and Trademark Office, Advisory Action received for U.S. Appl. No. 16/816,460, dated Oct. 19, 2023, 3 pages, US.
United States Patent and Trademark Office, Non-Final Office Action received for U.S. Appl. No. 17/162,461, dated Oct. 19, 2023, 25 pages, US.
United States Patent and Trademark Office, Advisory Action received for U.S. Appl. No. 17/162,461, dated Aug. 24, 2023, 2 pages, US.
United States Patent and Trademark Office, Notice of Allowance received for U.S. Appl. No. 16/552,021, dated Oct. 20, 2022, 14 pages, U.S.
United States Patent and Trademark Office, Final Office Action received for U.S. Appl. No. 16/816,460, dated Aug. 10, 2023, 14 pages, U.S.
United States Patent and Trademark Office, Non-Final Office Action received for U.S. Appl. No. 17/144,426, dated Jul. 13, 2023, 17 pages, U.S.
United States Patent and Trademark Office, Non-Final Office Action received for U.S. Appl. No. 17/158,118, dated Jul. 13, 2023, 18 pages, U.S.
United States Patent and Trademark Office, Advisory Action received for U.S. Appl. No. 17/144,426, dated Mar. 21, 2024, 5 pages.
United States Patent and Trademark Office, Advisory Action received for U.S. Appl. No. 17/674,366, dated Mar. 22, 2024, 6 pages.
United States Patent and Trademark Office, Final Office Action received for U.S. Appl. No. 17/705,919, dated Feb. 28, 2024, 61 pages.
United States Patent and Trademark Office, Final Office Action received for U.S. Appl. No. 17/175,939, dated Mar. 1, 2024, 24 pages.
United States Patent and Trademark Office, Advisory Action received for U.S. Appl. No. 16/867,286, dated Feb. 6, 2023, 3 pages, US.
United States Patent and Trademark Office, Advisory Action received for U.S. Appl. No. 17/144,426, dated Mar. 3, 2023, 6 pages, US.
United States Patent and Trademark Office, Final Office Action received for U.S. Appl. No. 17/158,118, dated Mar. 3, 2023, 19 pages, US.
United States Patent and Trademark Office, Non-Final Office Action received for U.S. Appl. No. 17/846,373, dated Apr. 5, 2024, 76 pages.
Pharmacy Reject Codes NCPDP, 5 pages.

(56) References Cited

OTHER PUBLICATIONS

St. Vincent's first to use Birmingham startup's information system. The Birmingham News [Online] Apr. 11, 2005. URL: http://www.awarix.com.
St. Vincent's is Digital Flagship D. Lockridge; Birmingham Medical News [Online] Sep. 2005.
Two automatic identification technology, neither new in the sense if being recent developments . . . Patient Safety & Quality Healthcare [Online] August 2005_ URL: http://www_awarix.com.
Advisory Action for U.S. Appl. No. 14/193,294 mailed Nov. 9, 2017, 3 pages.
Advisory Action for U.S. Appl. No. 15/085,166 dated Apr. 11, 2019, 4 pages.
Advisory Action for U.S. Appl. No. 15/085,166 dated Apr. 29, 2020, 3 pages.
Advisory Action for U.S. Appl. No. 15/137,371 mailed Feb. 25, 2019, 5 pages.
Advisory Action for U.S. Appl. No. 15/427,746 mailed Jul. 2, 2019, 2 pages.
Advisory Action received for U.S. Appl. No. 15/085,166, dated Jan. 29, 2021, 3 pages, US.
Almaro, Moshe; "Recovery and Reuse of Unused Prescription Drugs" MIT What Matters: Aug. 2005.
American Society of Health-System Pharmacists (ASHP), "Is Prescribing the Next Step in the Evolution of Pharmacy?" May 15, 2012.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data, PR Newswire, Jul. 30, 2001, p. 1, New York, NY, USA.
Anonymous, TechRx Announces Successful Beta Deployment of T-Rex. PR Newswire. May 13, 2002.
Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central LTD, UK.
CMS Updates Drug Dashboards with Prescription Drug Pricing and Spending Data, Data, Medicare Part D, Prescription drugs (Mar. 14, 2019).
Consalvo, Bob; "City of Boston in the City Council" hearing notice, Dec. 6, 2006.
Coping with Information Overload. The News Source for Healthcare Information Technology [Online] Nov. 2004. URL: http://www.awarix.com.
Decision to Grant European Patent Application No. 13809457.8 dated May 18, 2017.
Examiner's Answer for U.S. Appl. No. 14/145,027 mailed Sep. 7, 2016, 27 pages.
Extended European Search Report for European Application No. 13809457.8 dated Apr. 15, 2016, 6 pages.
Final Office Action for U.S. Appl. No. 12/140,015 mailed Jan. 31, 2011, 10 pages.
Final Office Action for U.S. Appl. No. 12/415,062 mailed Oct. 6, 2011, 18 pages.
Final Office Action for U.S. Appl. No. 12/555,589 mailed Apr. 11, 2012, 17 pages.
Final Office Action for U.S. Appl. No. 12/560,071 mailed Aug. 28, 2015, 8 pages.
Final Office Action for U.S. Appl. No. 12/560,071 mailed Nov. 8, 2012, 11 pages.
Final Office Action for U.S. Appl. No. 12/570,982 mailed Apr. 11, 2014, 22 pages.
Final Office Action for U.S. Appl. No. 12/570,982 mailed Aug. 28, 2015, 10 pages.
Final Office Action for U.S. Appl. No. 12/570,982 mailed Jan. 17, 2013, 19 pages.
Final Office Action for U.S. Appl. No. 12/730,015 mailed Aug. 14, 2012, 10 pages.
Final Office Action for U.S. Appl. No. 12/978,898 mailed May 16, 2013, 16 pages.
Final Office Action for U.S. Appl. No. 13/721,890 mailed Jun. 24, 2015, 14 pages.
Final Office Action for U.S. Appl. No. 13/721,890 mailed Nov. 25, 2016, 12 pages.
Final Office Action for U.S. Appl. No. 13/782,909 mailed May 31, 2016, 18 pages.
Final Office Action for U.S. Appl. No. 13/782,909 mailed Oct. 6, 2015, 24 pages.
Final Office Action for U.S. Appl. No. 13/804,175 mailed Oct. 6, 2015, 6 pages.
Final Office Action for U.S. Appl. No. 13/827,676 mailed Jul. 13, 2015, 17 pages.
Final Office Action for U.S. Appl. No. 14/090,113 mailed Jan. 6, 2016, 18 pages.
Final Office Action for U.S. Appl. No. 14/090,122 mailed Apr. 22, 2016, 13 pages.
Final Office Action for U.S. Appl. No. 14/145,027 mailed Nov. 19, 2015, 12 pages.
Final Office Action for U.S. Appl. No. 14/193,294 mailed May 2, 2016, 29 pages.
Final Office Action for U.S. Appl. No. 14/218,326 mailed Jun. 30, 2016, 17 pages.
Final Office Action for U.S. Appl. No. 15/085,166, dated Dec. 4, 2020, 11 pages.
Final Office Action for U.S. Appl. No. 15/137,371 mailed Nov. 28, 2018, 24 pages.
Final Office Action for U.S. Appl. No. 15/427,746 mailed Apr. 15, 2019, 9 pages.
Google NPL (non-patent literature) Search on "pharmacy payment benefit copay NDC database", retrieved from the Internet at <https://scholar.google.com/scholar?hl=en&as_sdt=3,47&g-pharmacy+payment+benefit+copay+NDC+database> on Feb. 20, 2022 at 3:02 pm, 1 page.
Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.
Google Patents Search (including Web Search History, Prior Art Search Printable History Generator) on "pharmacy payment benefit copay NDC database) (prescription) (code) (refills) (error code) country:US before:filing:Dec. 31, 2013", retrieved from the Internet at <https://patents.google.com/?q=pharmacy+payment+benefit+copay+NDC+database&q-prescription&q=code&q=refills&q=error+code&country=US&before—filing:Dec. 31, 2013> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt=0%2C47&as_ylo=2010&as_yhi=2013&q-pharmacy+payment+benefit+copay+NDC+database+pres . . . > retrieved on Jun. 1, 2022, 3 pages.
How to Estimate the Cost of a Prescription. Pam Olson, Sr. Client Services Executive, Navitus Health Solutions (Year: 2015).
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-PRESCRIPTIONS, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 mailed Jan. 14, 2015, 11 pages.
Marie Chisholm et al. "Pharmaceutical Manufacturer Assistance Program." Arch Intern Med. vol. 162, Apr. 8, 2002.

(56) References Cited

OTHER PUBLICATIONS

Non-Final Office Action for U.S. Appl. No. 12/560,071 mailed Jun. 21, 2012, 11 pages.
Non-Final Office Action for U.S. Appl. No. 12/570,982 mailed Jun. 20, 2012, 10 pages.
Non-Final Office Action for U.S. Appl. No. 14/193,294 mailed Feb. 21, 2017, 32 pages.
Non-Final Office Action for U.S. Appl. No. 15/085,166 dated Jun. 12, 2020, 26 pages.
Non-Final Office Action for U.S. Appl. No. 16/180,915 dated Jun. 1, 2020, 40 pages.
Non-final Office Action for U.S. Appl. No. 12/140,015 mailed Oct. 8, 2010, 9 pages.
Non-final Office Action for U.S. Appl. No. 12/189,650 mailed Jan. 22, 2010, 11 pages.
Non-final Office Action for U.S. Appl. No. 12/189,654 mailed Jan. 22, 2010, 11 pages.
Non-Final Office Action for U.S. Appl. No. 12/388,956 mailed Feb. 3, 2011, 11 pages.
Non-Final Office Action for U.S. Appl. No. 12/415,062 mailed Mar. 30, 2011, 23 pages.
Non-Final Office Action for U.S. Appl. No. 12/555,589 mailed Dec. 9, 2011, 12 pages.
Non-Final Office Action for U.S. Appl. No. 12/560,071 mailed Sep. 23, 2014, 17 pages.
Non-Final Office Action for U.S. Appl. No. 12/570,982 mailed Sep. 12, 2013, 22 pages.
Non-Final Office Action for U.S. Appl. No. 12/730,015 mailed Mar. 6, 2012, 9 pages.
Non-Final Office Action for U.S. Appl. No. 12/956,411 mailed Jan. 24, 2011, 9 pages.
Non-Final Office Action for U.S. Appl. No. 12/978,898 mailed Feb. 6, 2013, 12 pages.
Non-Final Office Action for U.S. Appl. No. 12/982,395 mailed Dec. 11, 2012, 13 pages.
Non-Final Office Action for U.S. Appl. No. 13/721,890 mailed Jan. 9, 2015, 11 pages.
Non-Final Office Action for U.S. Appl. No. 13/721,890 mailed Jun. 14, 2016, 9 pages.
Non-final Office Action for U.S. Appl. No. 13/782,909 mailed Feb. 11, 2016, 17 pages.
Non-Final Office Action for U.S. Appl. No. 13/827,676 mailed Dec. 26, 2014, 13 pages.
Non-final Office Action for U.S. Appl. No. 13/827,676 mailed Dec. 30, 2015, 23 pages.
Non-Final Office Action for U.S. Appl. No. 14/145,027 mailed Mar. 23, 2015, 13 pages.
Non-Final Office Action for U.S. Appl. No. 15/137,371 mailed May 29, 2018, 19 pages.
Non-Final Office Action for U.S. Appl. No. 15/427,746 mailed Oct. 18, 2018, 9 pages.
Non-Final Office Action for U.S. Appl. No. 16/819,258 dated Sep. 4, 2020, 6 pages.
Non-Final Office Action received for U.S. Appl. No. 15/085,166, dated Mar. 17, 2021, 11 pages.
Non-Final Office Action received for U.S. Appl. No. 16/551,962, dated Mar. 2, 2021, 16 pages.
Non-Final Office Action received for U.S. Appl. No. 16/453,509 mailed Mar. 26, 2021, 45 pages.
Non-Final Office Action received for U.S. Appl. No. 16/832,318 mailed Apr. 23, 2021, 52 pages.
Notice of Allowance and Fees(s) Due for U.S. Appl. No. 15/925,011 dated Jan. 22, 2021, 15 pages.
Notice of Allowance for U.S. Appl. No. 16/180,915 dated Dec. 11, 2020, 23 pages.
Notice of Allowance for U.S. Appl. No. 11/674,069 mailed Jul. 19, 2010, 13 pages.
Notice of Allowance for U.S. Appl. No. 12/140,015 mailed Jun. 10, 2011, 10 pages.
Notice of Allowance for U.S. Appl. No. 12/165,221 mailed Nov. 16, 2010, 6 pages.
Notice of Allowance for U.S. Appl. No. 12/189,650 mailed Aug. 13, 2010, 11 pages.
Notice of Allowance for U.S. Appl. No. 12/388,956 mailed Jun. 14, 2011, 9 pages.
Notice of Allowance for U.S. Appl. No. 12/956,411 mailed Aug. 5, 2011, 8 pages.
Notice of Allowance for U.S. Appl. No. 12/982,395 mailed Apr. 24, 2013, 9 pages.
Notice of Allowance for U.S. Appl. No. 14/181,011 dated May 15, 2019, 9 pages.
Notice of Allowance for U.S. Appl. No. 15/137,371 mailed May 2, 2019, 11 pages.
Notice of Allowance for U.S. Appl. No. 15/427,746 mailed Dec. 4, 2019, 5 pages.
Notice of Allowance for U.S. Appl. No. 15/427,746 mailed Jul. 31, 2019, 8 pages.
Notice of Allowance received for U.S. Appl. No. 14/643,468, filed Oct. 24, 2018, 22 pages.
Notice of Allowance received for U.S. Appl. No. 14/181,011, filed Feb. 13, 2019, 9 pages.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/193,294 dated Sep. 19, 2018, 27 pages.
Office Action for U.S. Appl. No. 14/229,043 dated Feb. 27, 2019, 18 pages.
Office Action for U.S. Appl. No. 14/229,043 dated Jul. 24, 2017, 19 pages.
Office Action for U.S. Appl. No. 14/229,043 dated Sep. 5, 2019, 22 pages.
Office Action for U.S. Appl. No. 14/229,043 dated Sep. 14, 2018, 17 pages.
Office Action for U.S. Appl. No. 14/643,468 dated Mar. 8, 2018, 11 pages.
Office Action for U.S. Appl. No. 15/085,166 dated Dec. 27, 2018, 24 pages.
Office Action for U.S. Appl. No. 15/085,166 dated Jun. 29, 2018, 19 pages.
Office Action for U.S. Appl. No. 15/085,166 dated Mar. 3, 2020, 25 pages.
Office Action for U.S. Appl. No. 15/085,166 dated Sep. 4, 2019, 23 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
Office Action for U.S. Appl. No. 12/570,982 mailed Apr. 8, 2015, 9 pages.
Office Action for U.S. Appl. No. 13/782,909 mailed Jun. 25, 2015, 16 pages.
Office Action for U.S. Appl. No. 13/804,175 mailed Mar. 13, 2015, 9 pages.
Office Action for U.S. Appl. No. 14/090,113 mailed Jun. 18, 2015, 14 pages.
Office Action for U.S. Appl. No. 14/090,122 mailed Oct. 21, 2016, 12 pages.

(56) References Cited

OTHER PUBLICATIONS

Office Action for U.S. Appl. No. 14/090,122 mailed Sep. 11, 2015, 10 pages.
Office Action for U.S. Appl. No. 14/181,011 mailed Feb. 29, 2016, 23 pages.
Office Action for U.S. Appl. No. 14/181,011 mailed Mar. 20, 2017, 28 pages.
Office Action for U.S. Appl. No. 14/181,011 mailed Oct. 20, 2016, 28 pages.
Office Action for U.S. Appl. No. 14/181,011 mailed Sep. 12, 2017, 17 pages.
Office Action for U.S. Appl. No. 14/193,294 mailed Dec. 17, 2015, 21 pages.
Office Action for U.S. Appl. No. 14/218,326 mailed Dec. 1, 2015, 13 pages.
Opar, Alisa; "Rising drug costs prompt new uses for old pills." Nature Medicine, 1211333 (2006).
PTAB Decision on Appeal for U.S. Appl. No. 14/145,027 mailed May 31, 2018, 11 pages.
PTAB Decision on Request for Rehearing for U.S. Appl. No. 14/145,027 mailed Aug. 30, 2018, 9 pages.
Sampson, R.J., Taking Control of Health Care Costs, Best's Review—Life Health Insurance Edition, Nov. 1983, vol. 84, Issue 7, USA; Abstract only.
Scientific and Technical Information Center, Report of Information from Dialog (NPL (non-patent literature) Search Results, Abstracts only), dated Nov. 1, 2021, (Year: 2021), 9 pages.
Siler, Sharon et al., "Safe Disposal of Unused Controlled Substances" Avalere Health 2008.
Strom, Stephanie; "Old Pills Finding New Medicine Cabinets" NY Times, May 18, 2005.
Subnotebooks, Phones, and More. St. Vincent's Gets on Track. Mobile Health Data [Online], Nov. 19, 2004. URL:http://www.awarix.com.
Supplemental Notice of Allowability received for U.S. Appl. No. 16/180,915, dated Jan. 28, 2021, 2 pages.
Supplemental Notice of Allowability received for U.S. Appl. No. 16/180,915, dated Mar. 12, 2021, 10 pages.
U.S. Notice of Allowance received for U.S. Appl. No. 16/819,258, dated Nov. 16, 2020, 8 pages, U.S.
U.S. Appl. No. 14/229,043, "Systems And Methods For Monitoring And Reporting Redemption Information At A Pharmacy For Patient Incentive Information Identified At The Time Of Prescribing," Unpublished (Filed Mar. 28, 2014), (Roger Pinsonneault, Inventor), (Mckesson Corporation, Assignee), abandoned.
U.S. Appl. No. 15/084,034, "Prescription Provider System," Unpublished (Filed Mar. 29, 2016), (Scott Genone, Inventor), (McKesson Corporation, Assignee), abandoned.
U.S. Appl. No. 15/085,166, "Alternative Therapy Identification System", Unpublished (Filed Mar. 30, 2016), (Elizabeth Kaye, Inventor), (Mckesson Corporation, Assignee), pending.
U.S. Appl. No. 16/832,318, "Method, Apparatus, And Computer Program Product for Estimated Prescription Costs", Unpublished (Filed Mar. 27, 2020), (Stacy Hopkins, Inventor), (Mckesson Corporation, Assignee), pending.
U.S. Appl. No. 17/012,565, "Method, Apparatus, and Computer Program Product for Performing an Alternative Evaluation Procedure in Response to an Electronic Message," Unpublished (filing date Sep. 4, 2020), (Stacy Hopkins, et al., Inventors) (McKesson Corporation, Assignee), pending.
U.S. Appl. No. 17/092,705, "Computing System and Method for Automatically Reversing an Action Indicated by an Electronic Message," Unpublished (filing date Nov. 9, 2020), (Patrick Harris, Inventor) (McKesson Corporation, Assignee), pending.
U.S. Appl. No. 16/792,413, "Method, Apparatus and Computer Program Product for Partitioning Prescription Transaction Costs in an Electronic Prescription Transaction," Unpublished (filed Feb. 17, 2020), (Jared Burdine, Inventor) (McKesson Corporation, Assignee), pending.
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee), pending.
U.S. Appl. No. 17/175,939, "Method, Apparatus, And Computer Program Product For Generating Inquiries In Different Formats, And Compiling Different Information Types In A Response," Unpublished (filed Feb. 15, 2021), (Stacy Hopkins, et al., Inventor) (Mckesson Corporation, Assignee), pending.
U.S. Appl. No. 16/453,509, "Method, Apparatus, And Computer Program Product For Providing Estimated Prescription Costs," Unpublished (filed Jun. 26, 2019), (Stacy Hopkins, et al., Inventor) (Mckesson Corporation, Assignee), pending.
U.S. Appl. No. 17/499,976, "Method, Apparatus, And Computer Program Product For Providing Real-Time Pricing Information," Unpublished (filed Oct. 13, 2021), (Stacy Hopkins, et al., Inventor) (Mckesson Corporation, Assignee), pending.
U.S. Appl. No. 17/501,532, "Method, Apparatus, And Computer Program Product For Providing Real-Time Pricing Information," Unpublished (filed Oct. 14, 2021), (Keith Crozier, et al., Inventor) (Mckesson Corporation, Assignee), pending.
U.S. Appl. No. 17/219,526, "Method And Apparatus For Parsing And Differently Processing Different Portions Of A Request," Unpublished (filed Mar. 31, 2021), (Melissa Frechen, et al., Inventor) (Mckesson Corporation, Assignee), pending.
U.S. Appl. No. 17/162,461, "Method, Apparatus, And Computer Program Product For Constructing Electronic Message Responses Dependent Upon Historical Information," Unpublished (filed Jan. 19, 2021), (Stewart Aragon, et al., Inventor) (McKesson Corporation, Assignee), pending.
U.S. Appl. No. 17/144,426, "Method, Apparatus, And Computer Program Product For Estimating A Target Quantitative Measure Based Upon Historical Electronic Messages," Unpublished (filed Jan. 8, 2021), (Stewart Aragon, et al., Inventor) (McKesson Corporation, Assignee), pending.
U.S. Appl. No. 17/158,118, "Method, Apparatus, And Computer Program Product For Estimating A Target Quantitative Measure Based Upon Historical Electronic Messages," Unpublished (filed Jan. 26, 2021), (Stewart Aragon, et al., Inventor) (McKesson Corporation, Assignee), pending.
U.S. Appl. No. 17/676,437, "Method, Apparatus, And Computer Program Product For Partitioning Prescription Transaction Costs In An Electronic Prescription Transaction," Unpublished (filed Feb. 21, 2022), (Phillip Draa, et al., Inventor) (McKesson Corporation, Assignee), pending.
U.S. Appl. No. 17/705,919, "Method, Apparatus, And Computer Program Product For Generating Alternative Evaluation Messages," Unpublished (filed Mar. 28, 2022), (Stacy Hopkins, et al., Inventor) (McKesson Corporation, Assignee), pending.
United States Patent and Trademark Office, Advisory Action for U.S. Appl. No. 15/422,184, Jun. 25, 2019, 4 pages, U.S.A.
United States Patent and Trademark Office, Advisory Action for U.S. Appl. No. 15/422,184, filed Mar. 26, 2020, 5 pages, U.S.A.
United States Patent and Trademark Office, Advisory Action for U.S. Appl. No. 15/925,011, filed Jan. 31, 2020, 3 pages, U.S.A.
United States Patent and Trademark Office, Advisory Action for U.S. Appl. No. 15/925,948, filed Jan. 31, 2020, 4 pages, U.S.A.
United States Patent and Trademark Office, Advisory Action received for U.S. Appl. No. 16/453,509, dated Oct. 12, 2021, 5 pages, U.S.
United States Patent and Trademark Office, Advisory Action received for U.S. Appl. No. 16/832,318, dated Jan. 28, 2022, 4 pages, U.S.
United States Patent and Trademark Office, Advisory Action received for U.S. Appl. No. 16/792,413, dated Mar. 10, 2022, 4 pages, US.
United States Patent and Trademark Office, Corrected Notice of Allowability received for U.S. Appl. No. 15/085,166, dated Sep. 20, 2021, 6 pages, U.S.
United States Patent and Trademark Office, Final Office Action received for U.S. Appl. No. 16/453,509, dated Aug. 18, 2021, 16 pages, U.S.
United States Patent and Trademark Office, Final Office Action received for U.S. Appl. No. 16/551,962, dated Nov. 4, 2021, 32 pages, U.S.

(56) References Cited

OTHER PUBLICATIONS

United States Patent and Trademark Office, Final Office Action received for U.S. Appl. No. 16/832,318, dated Nov. 3, 2021, 22 pages, U.S.
United States Patent and Trademark Office, Final Office Action received for U.S. Appl. No. 16/792,413, dated Jan. 10, 2022, 80 pages, U.S.
United States Patent and Trademark Office, Non-Final Office Action received for U.S. Appl. No. 16/792,413, dated Aug. 5, 2021, 32 pages, U.S.
United States Patent and Trademark Office, Non-Final Office Action received for U.S. Appl. No. 15/085,166, dated Jan. 10, 2022, 12 pages, U.S.
United States Patent and Trademark Office, Non-Final Office Action received for U.S. Appl. No. 16/867,286, dated Feb. 22, 2022, 38 pages, U.S.
United States Patent and Trademark Office, Non-Final Office Action received for U.S. Appl. No. 17/012,565, dated Apr. 12, 2022, 19 pages, U.S.A.
United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 16/552,021, dated May 3, 2022, 60 pages, U.S.A.
United States Patent and Trademark Office, Non-Final Office Action received for U.S. Appl. No. 17/175,939, dated May 12, 2022, 48 pages, U.S.A.
United States Patent and Trademark Office, Non-Final Office Action received for U.S. Appl. No. 16/792,413, dated May 24, 2022, 48 pages, US.
United States Patent and Trademark Office, Non-Final Office Action received for U.S. Appl. No. 17/144,426, dated May 31, 2022, 42 pages, US.
United States Patent and Trademark Office, Non-Final Office Action received for U.S. Appl. No. 16/832,318, dated Jun. 8, 2022, 17 pages, US.
United States Patent and Trademark Office, Notice of Allowability received for U.S. Appl. No. 15/422,184, filed Nov. 16, 2020, 2 pages, U.S.A.
United States Patent and Trademark Office, Notice of Allowance and Fee(s) Due received for U.S. Appl. No. 17/219,526, dated Mar. 22, 2022, 11 pages, US.
United States Patent and Trademark Office, Notice of Allowance and Fee(s) Due received for U.S. Appl. No. 16/551,962, dated Mar. 16, 2022, 10 pages, US.
United States Patent and Trademark Office, Notice of Allowance and Fee(s) Due received for U.S. Appl. No. 17/092,705, dated Mar. 24, 2022, 9 pages, US.
United States Patent and Trademark Office, Notice of Allowance and Fee(s) Due received for U.S. Appl. No. 16/551,962, dated Mar. 1, 2022, 14 pages, US.
United States Patent and Trademark Office, Notice of Allowance received for U.S. Appl. No. 15/422,184, filed Oct. 13, 2020, 12 pages, U.S.A.
United States Patent and Trademark Office, Notice of Allowance received for U.S. Appl. No. 15/925,948, filed Nov. 5, 2020, 22 pages, U.S.A.
United States Patent and Trademark Office, Notice of Allowance received for U.S. Appl. No. 15/085,166, dated Sep. 10, 2021, 21 pages, U.S.
United States Patent and Trademark Office, Notice of Allowance received for U.S. Appl. No. 15/085,166, dated Jun. 15, 2022, 18 pages, U.S.
United States Patent and Trademark Office, Notice of Allowance received for U.S. Appl. No. 17/092,705, dated Dec. 23, 2021, 42 pages, U.S.
United States Patent and Trademark Office, Notice of Allowance received for U.S. Appl. No. 16/043,401, dated Aug. 10, 2020, 9 pages, U.S.A.
United States Patent and Trademark Office, Notice of Allowance received for U.S. Appl. No. 17/219,526, dated Feb. 3, 2022, 48 pages, U.S.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.
United States Patent and Trademark Office, Notice of Allowance received for U.S. Appl. No. 16/551,962, dated Jun. 8, 2022, 11 pages, US.
United States Patent and Trademark Office, Office Action for U.S. Appl. No. 15/925,011, filed Apr. 8, 2020, 17 pages, U.S.A.
United States Patent and Trademark Office, Office Action for U.S. Appl. No. 15/925,948, filed Mar. 23, 2020, 29 pages, U.S.A.
United States Patent and Trademark Office, Office Action received for U.S. Appl. No. 15/422,184, filed May 18, 2020, 31 pages, U.S.A.
United States Patent and Trademark Office, Office Action received for U.S. Appl. No. 15/925,011, filed Oct. 8, 2020, 8 pages, U.S.A.
Wisconsin Physicians Service (WPS) Insurance Corporation, "How to Read Your Explanation of Benefits Chart," Jun. 16, 2012.
www.ncoil.org/news/DrugCards2.doc dated Apr. 2002, 5 pages.
Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.
U.S. Appl. No. 16/792,413, filed Feb. 17, 2020, None, Pending.
American Hospital Association, "Drug Price Proposals", dated Apr. 2019, retrieved from the Internet at <URL: https://www.aha.org/system/files/media/file/2019/04/aha-drug-policy-recommendations_2.pdf>, 8 pages.
California Health Care Foundation, "When the Price Is Not Right: State Options on Prescription Drug Pricing", dated Jun. 2016, retrieved from the Internet at: <URL: https://www.chcf.org/wp-content/uploads/2017/12/PDF-WhenStateRxPricing.pdf>, 16 pages.
Hsee, Christopher K., et al., "General Evaluability Theory", Perspectives on Psychological Science, Jul. 2010, pp. 343-355, vol. 5, No. 4, Sage Publications, Inc. on behalf of the Association for Psychological Science retrieved from the Internet at <URL: https://www.jstor.org/stable/41613442>.
United States Patent and Trademark Office, Advisory Action received for U.S. Appl. No. 16/867,286, dated Dec. 6, 2022, 8 pages, US.
United States Patent and Trademark Office, Advisory Action received for U.S. Appl. No. 17/175,939, dated Dec. 22, 2022, 5 pages, US.
United States Patent and Trademark Office, Final Office Action received for U.S. Appl. No. 17/144,426, dated Dec. 8, 2022, 21 pages, US.
United States Patent and Trademark Office, Notice of Allowance received for U.S. Appl. No. 16/832,318, dated Dec. 8, 2022, 26 pages, US.
Van Nuys, Ph.D., Karen, et al., "Prescription Drug Copayment Coupon Landscape", Drug Pricing White Paper, USC Leonard D. Schaeffer Center for Health Policy and Economics, Feb. 7, 2018, retrieved from the Internet at <URL: https://healthpolicy.usc.edu/research/prescription-drug-copayment-coupon-landscape/>, 21 pages.
United States Patent and Trademark Office, Final Office Action received for U.S. Appl. No. 16/816,460, dated May 3, 2024, 22 pages, U.S.
United States Patent and Trademark Office, Non-Final Office Action received for U.S. Appl. No. 17/676,437, dated May 9, 2024, 73 pages, U.S.
United States Patent and Trademark Office, Non-Final Office Action received for U.S. Appl. No. 17/674,366, dated Jun. 5, 2024, 54 pages, US.
United States Patent and Trademark Office, Final Office Action received for U.S. Appl. No. 17/162,461, dated Jun. 4, 2024, 38 pages, US.
Coase, R. H., "The Nature of the Firm", Economica, Nov. 1937, pp. 386-405, vol. 4, No. 16, Blackwell Publishing for London School of Economics and Political Science, retrieved from the Internet at http://www.jstor.org/stable/2626876 on Nov. 7, 2011.

(56) References Cited

OTHER PUBLICATIONS

Gemmill, Marin, "The price elasticity of demand for prescription drugs: An exploration of demand in different settings", Doctor of Philosophy Thesis submitted to the London School of Economics and Political Science, Jan. 2008, 380 pages, UMI No. U615895, UMI Dissertation Publishing, ProQuest LLC, US.

United States Patent and Trademark Office, Advisory Action and Examiner-Initiated Interview Summary received for U.S. Appl. No. 17/705,919, dated Jun. 25, 2024, 33 pages, US.

United States Patent and Trademark Office, Examiner's Answer received for U.S. Appl. No. 16/867,286, dated Jun. 28, 2024, 9 pages, US.

United States Patent and Trademark Office, Non-Final Office Action received for U.S. Appl. No. 17/144,426, dated Jul. 18, 2024, 19 pages, US.

United States Patent and Trademark Office, Non-Final Office Action received for U.S. Appl. No. 17/158,118, dated Jul. 18, 2024, 22 pages, US.

United States Patent and Trademark Office, Notice of Allowance received for U.S. Appl. No. 17/846,373, dated Jul. 25, 2024, 16 pages, US.

United States Patent and Trademark Office, Advisory Action received for U.S. Appl. No. 16/816,460, dated Aug. 1, 2024, 3 pages, U.S.

United States Patent and Trademark Office, Advisory Action received for U.S. Appl. No. 17/162,461, dated Aug. 19, 2024, 2 pages, U.S.

United States Patent and Trademark Office, Non-Final Office Action received for U.S. Appl. No. 18/098,150, dated Aug. 27, 2024, 61 pages, U.S.

Tiriveedhi, V., "Impact of Precision Medicine on Drug Repositioning and Pricing: A Too Small to Thrive Crisis", Journal of Personalized Medicine, Nov. 5, 2018, 11 pages, vol. 8, No. 36, MDPI, Switzerland.

United States Patent and Trademark Office, Notice of Allowance received for U.S. Appl. No. 17/705,919, dated Sep. 3, 2024, 13 pages, USA.

United States Patent and Trademark Office, Notice of Allowance received for U.S. Appl. No. 17/676,437, dated Sep. 25, 2024, 20 pages, USA.

United States Patent and Trademark Office, Examiner Interview Summary received for U.S. Appl. No. 17/144,426, dated Oct. 22, 2024, 8 pages, U.S.

United States Patent and Trademark Office, Examiner Interview Summary received for U.S. Appl. No. 17/158,118, dated Oct. 22, 2024, 8 pages, U.S.

United States Patent and Trademark Office, Non-Final Office Action received for U.S. Appl. No. 17/501,532, dated Oct. 17, 2024, 37 pages, U.S.

United States Patent and Trademark Office, Non-Final Office Action received for U.S. Appl. No. 17/499,976, dated Oct. 1, 2024, 79 pages, U.S.

United States Patent and Trademark Office, Non-Final Office Action received for U.S. Appl. No. 17/175,939, dated Oct. 24, 2024, 17 pages, U.S.

United States Patent and Trademark Office, Examiner Interview Summary received for U.S. Appl. No. 18/098,150, dated Nov. 18, 2024, 3 pages, U.S.

United States Patent and Trademark Office, Non-Final Office Action received for U.S. Appl. No. 16/816,460, dated Nov. 21, 2024, 28 pages, US.

United States Patent and Trademark Office, Examiner Interview Summary received for U.S. Appl. No. 17/175,939, dated Dec. 3, 2024, 2 pages, US.

United States Patent and Trademark Office, Final Office Action received for U.S. Appl. No. 17/144,426, dated Dec. 19, 2024, 22 pages, U.S.

United States Patent and Trademark Office, Final Office Action received for U.S. Appl. No. 17/158,118, dated Dec. 19, 2024, 24 pages, US.

* cited by examiner

METHOD, APPARATUS, AND COMPUTER PROGRAM PRODUCT FOR REFORMATTING AN ELECTRONIC PRESCRIPTION TRANSACTION

CROSS REFERENCE TO RELATED APPLICATION

This application is a continuation-in-part of, and claims priority to U.S. patent application Ser. No. 16/792,413 filed Feb. 17, 2020, and entitled METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION, the entire contents of which is hereby incorporated by reference.

TECHNOLOGICAL FIELD

Embodiments of the present invention relate generally to prescription transactions and, more particularly, to methods, apparatuses, and computer program products for partitioning prescription transaction costs in an electronic prescription transaction, by determining a credit amount to be applied to the electronic prescription transaction based on an alternative cash price.

BACKGROUND

Prior authorization for prescription claims requires that a payer, such as an insurance plan and/or the like, approve the prescription prior to the patient obtaining the prescription and/or prior to agreement the prescription will be covered under the plan. Often times, an initial request, or even subsequent requests, for prior authorization for a prescription are denied and require further input or information be provided by the healthcare provider. In some instances, the payer does so to ensure the prescription is medically necessary, and/or to determine whether an alternative therapy may be used. As the price of prescription drugs continue to increase, and the number of prescription options and alternatives increase, prior authorization requirements are becoming more common, as the payer seeks cost-effective therapy for patients.

However, in many circumstances, the prior authorization process slows down or prevents the patient from obtaining their prescribed medication. Lag time between communications, review, and input by the healthcare provider, pharmacy, and/or payer may further delay or prevent the patient from obtaining the prescription. For example, obtaining prior authorization from a prescription benefit plan may require 12 hours or up to as many as 5 business days or more. In some cases, patients may become frustrated to the extent of abandoning any prescription therapy altogether.

Some pharmaceutical manufacturers offer rebates, copay assistance, or credits toward the purchase of certain prescription drugs, to encourage patients to adhere to their prescription, compete in the market with alternative medications, and/or the like. In some instances, a service provider computer may be authorized by a pharmaceutical manufacturer to distribute rebates, or credits, toward the cost of prescription drugs, as the service provider determines such that some transactions and/or patient may receive different rebate amounts, even for the same prescription drug. The service provider computer may automatically determine credit amounts in real-time or near real-time as prescription transactions and inquiries and submitted via a pharmacy.

BRIEF SUMMARY

Methods, apparatuses, and computer program products are therefore provided for partitioning costs of prescription transactions by determining a credit amount to be applied to a prescription transaction, based on an alternative cash price, and according to example embodiments provided herein. An apparatus is provided, comprising at least one processor and at least one memory including computer program code, the at least one memory and the computer program code configured to, with the processor, cause the apparatus to at least receive an indication of a prescription transaction comprising a patient identifier identifying a patient, a prescription identifier identifying a drug, and benefit information. The at least one memory and the computer program code are further configured to, with the processor, cause the apparatus to determine the prescription transaction is classified a first classification of at least two classifications of prescription transactions. In response to determining the prescription transaction is classified as the first classification, the at least one memory and the computer program code are further configured to, with the processor, cause the apparatus to determine a cash price of the drug. Further in response to determining the prescription transaction is classified as the first classification, the at least one memory and the computer program code are further configured to, with the processor, cause the apparatus to determine a credit amount to be applied to the cash price. The at least one memory and the computer program code are further configured to, with the processor, cause the apparatus to reformat the prescription transaction to a format that indicates a cash transaction and the credit amount. The at least one memory and the computer program code are further configured to, with the processor, cause the apparatus to cause transmission of the reformatted prescription transaction including the indication of the cash transaction and the credit amount.

The first classification comprises an indication that a prescription benefit claim associated with the prescription transaction is at least one of denied or likely to be denied. The prescription transaction is denied or determined to likely be denied based on a requirement for prior authorization. The cash price of the drug may be determined based on contractual pricing associated with a manufacturer. The prescription transaction is received from at least one of a pharmacy computer, an adjudication computer, or a prescriber computer. The reformatted prescription transaction is transmitted to at least one of a pharmacy computer, an adjudication computer, or a prescriber computer. The cash price of the drug may be determined based on accessing data provided by a provider of a cash discount system. The at least one memory and the computer program code may be further configured to, with the processor, cause the apparatus to at least transmit the credit amount to a third party computer.

A method is provided, including receiving an indication of a prescription transaction comprising a patient identifier identifying a patient, a prescription identifier identifying a drug, and benefit information. The method may further include determining the prescription transaction is classified a first classification of at least two classifications of prescription transactions. In response to determining the prescription transaction is classified as the first classification, the method includes determining a cash price of the drug, and determining a credit amount to be applied to the cash price. The method further include reformatting the prescription transaction to a format that indicates a cash transaction and the credit amount, and causing transmission of the reformatted prescription transaction including the indication of the cash transaction and the credit amount.

A computer program product is provided, comprising at least one non-transitory computer-readable storage medium having computer-executable program code instructions stored therein, the computer-executable program code instructions comprising program code instructions to receive an indication of a prescription transaction comprising a patient identifier identifying a patient, a prescription identifier identifying a drug, and benefit information. The computer-executable program code instructions further include program code instructions to determine the prescription transaction is classified a first classification of at least two classifications of prescription transactions. In response to determining the prescription transaction is classified as the first classification, the computer-executable program code instructions further include program code instructions to determine a cash price of the drug, and to determine a credit amount to be applied to the cash price. The computer-executable program code instructions further include program code instructions to reformat the prescription transaction to a format that indicates a cash transaction and the credit amount. The computer-executable program code instructions further include program code instructions to cause transmission of the reformatted prescription transaction including the indication of the cash transaction and the credit amount.

An apparatus is provided, including means for receiving an indication of a prescription transaction comprising a patient identifier identifying a patient, a prescription identifier identifying a drug, and benefit information. The apparatus may further include means for determining the prescription transaction is classified a first classification of at least two classifications of prescription transactions. In response to determining the prescription transaction is classified as the first classification, the apparatus includes means for determining a cash price of the drug, and means for determining a credit amount to be applied to the cash price. The apparatus further includes means for reformatting the prescription transaction to a format that indicates a cash transaction and the credit amount, and means for causing transmission of the reformatted prescription transaction including the indication of the cash transaction and the credit amount.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
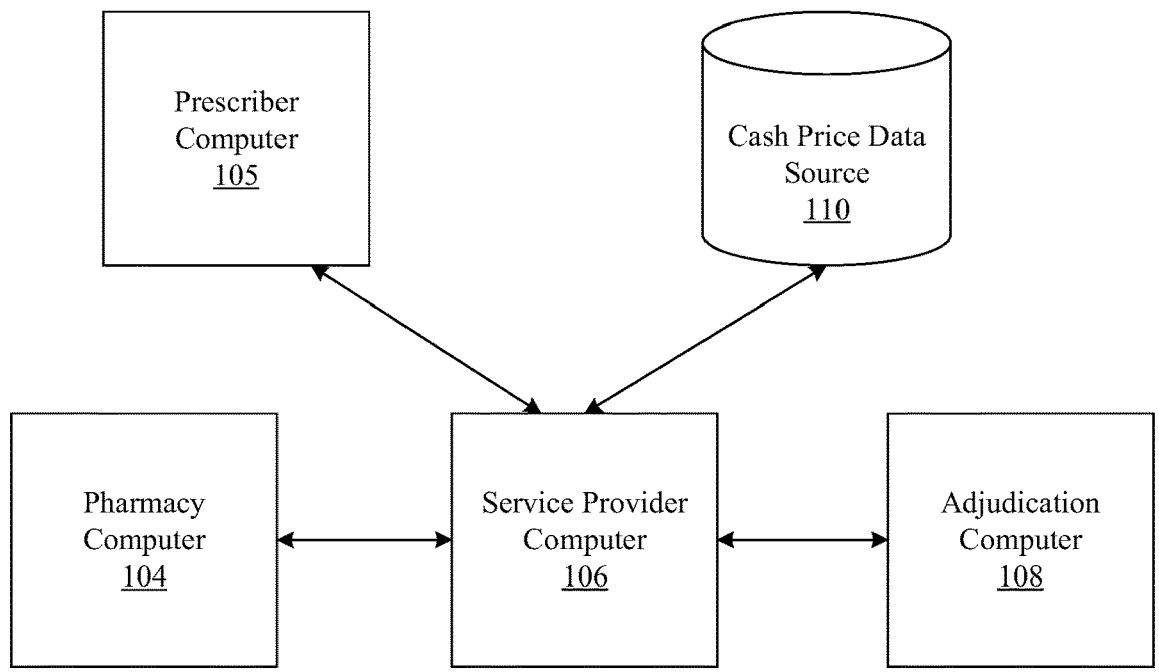
Figure 2:
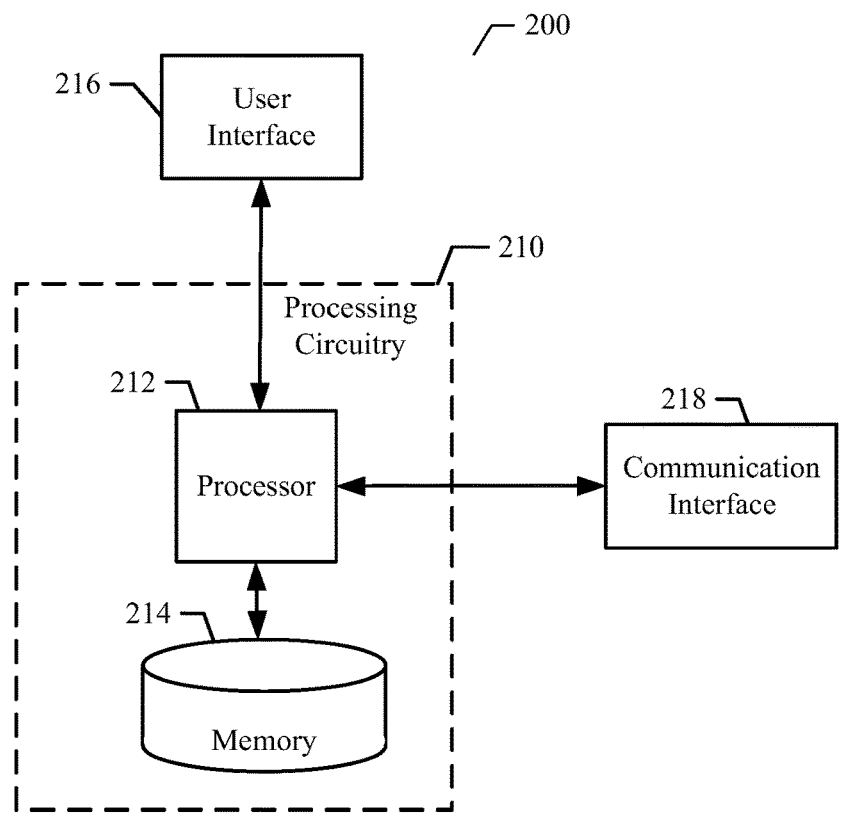
Figure 3:
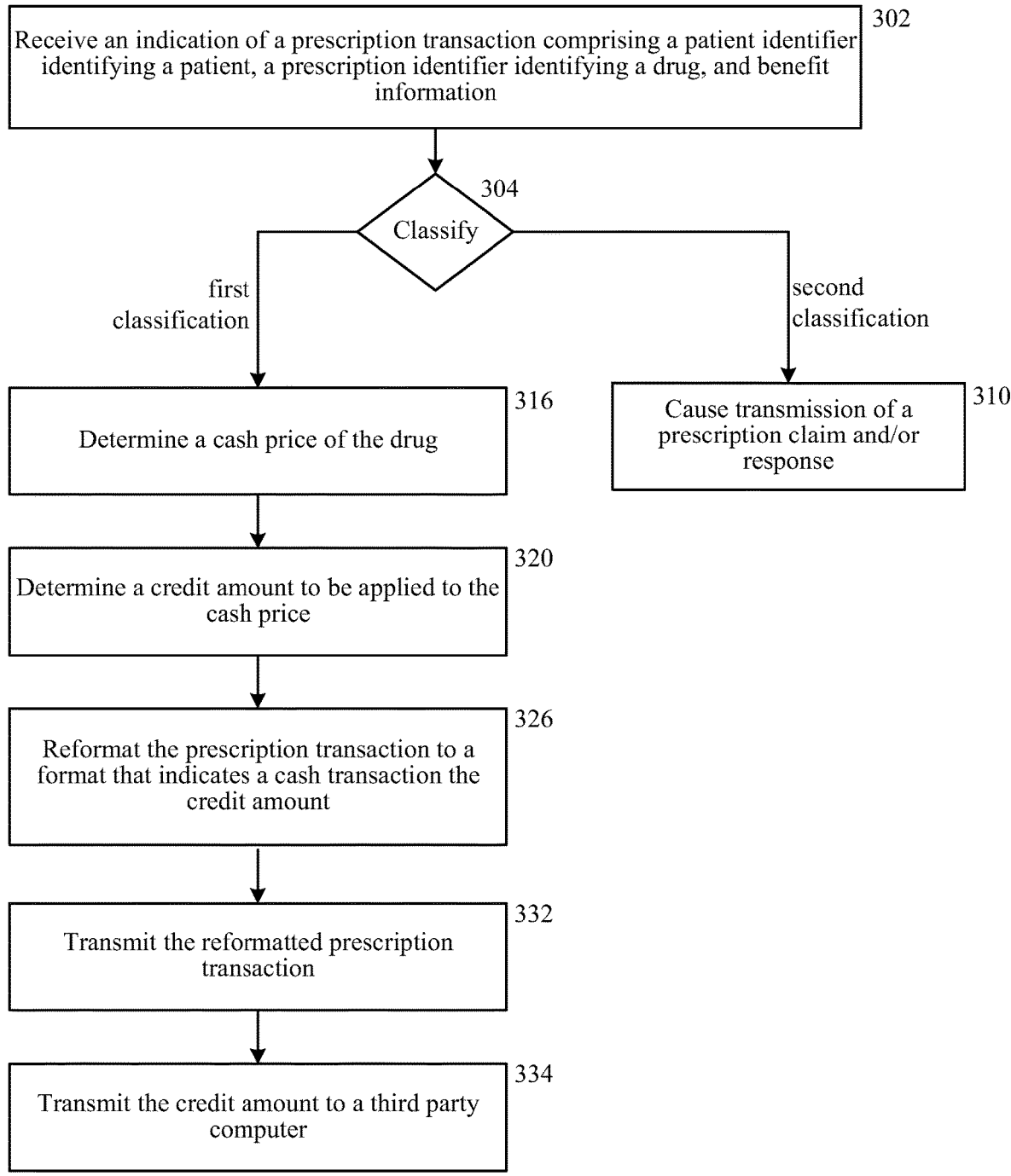

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIG. 3 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to partition prescription transaction costs by determining a credit amount to be applied to a prescription transaction, based on an alternative cash price, and according to certain example embodiments described herein. The pharmacy computer 104 may be associated with a pharmacy or pharmacy network to facilitate the filling of prescriptions, transmitting prescription claims to a service provider computer 106, and/or the like. The pharmacy computer 104 may additionally or alternatively be associated with a physician's office, clinic, long-term care facility, hospital, etc. Accordingly, while the exemplary pharmacy computer 104 may be frequently referenced herein as part of a pharmacy or pharmacy network, the pharmacy computer 104 may be associated with any other healthcare provider, such as a physician's office, hospital and/or other medical facility.

The pharmacy computer 104 may be any processor-driven device that facilitates the submission of prescription transaction requests made by patients or consumers and the communication of information associated with prescription transactions to the service provider computer 106. In certain example embodiments, the pharmacy computer 104 may be a point of sale device associated with a pharmacy. The execution of the computer-implemented instructions by the pharmacy computer 104 may form a special purpose computer or other particular machine that is operable to facilitate the submission of pharmacy transaction requests made by patients, pharmacists, and/or the like, and the communication of information associated therewith to a service provider computer 106.

A prescriber computer 105 may be any processor-driven device that facilitates the submission of prescriptions, such as by a physician or other healthcare provider, to the service provider computer 106. The service provider computer 106 may further route prescriptions to a pharmacy computer 104 to be filled, and/or adjudication computer 108, to be adjudicated and/or processed for prior authorization. In certain embodiments, the prescriber 105 may be configured to receive a response from the service provider computer 106, and provide pricing information via a user interface during a patient encounter. In this regard, the pricing information may be provided in real-time or near real-time and may impact which medication is prescribed by a physician (such as based on affordability for a patient).

The service provider computer 106 may include, but is not limited to, a processor-driven device that is configured for receiving, processing, and fulfilling prescription requests from the pharmacy computer 104 and/or the adjudication computer 108 (described below), relating to prescription tracking, claims processing, benefits, billing, other healthcare transactions, and/or other related activities. Additionally or alternatively, the service provider computer 106 may be operable to facilitate the receipt, routing, and/or processing of healthcare transactions such as prescription transactions, prescription claims, and/or associated responses amongst various components and/or subsystems such as, but not limited to, those depicted in FIG. 1.

In certain exemplary embodiments, the service provider computer 106 may be configured as or may comprise a switch or router that evaluates, modifies, reformats, generates, and/or routes healthcare transactions such as prescription transactions. For example, the service provider computer 106 may route prescription transactions communicated from the pharmacy computer 104 to an adjudication computer 108, such as that associated with a pharmacy benefits manager (PBM), an insurer, a Medicare or other government healthcare insurance program payer, or other payer. According to certain embodiments, the adjudication computer 108 may comprise any other computer system that receives and adjudicates a prescription claim on behalf of the payer.

Additionally or alternatively, the service provider computer 106 may reformat healthcare transactions into another form of transaction and modify the recipient information of the reformatted transaction before routing the reformatted transaction to another party, such as adjudication computer 108. The service provider computer 106 may also optionally apply edits to at least some of the healthcare transactions.

The service provider computer 106 may transmit responses from the adjudication computer 108 regarding the prescription transaction to the pharmacy computer 104. For example, the service provider computer 106 may notify the pharmacy computer 104 that preauthorization is required, and that the claim is therefore at least initially rejected. As another example, in an instance of an adjudicated claim, the service provider computer 106 may notify the pharmacy computer 104 of a co-pay or out of pocket costs to be paid by the patient for the prescription and/or the benefit applied to the prescription transaction. In this regard, a message or other notification may be appended to or included in the response transmitted to the pharmacy computer 104, such as a reject code or reason indicating preauthorization is required, co-pay amounts, and/or the like. Any of the aforementioned responses may be provided to the pharmacy computer 104 together with a prescription transaction response, or the service provider computer 106 may reformat the prescription transaction to include the details of such responses and transmit the reformatted healthcare transaction to the pharmacy computer 104.

The service provider computer 106 may further include a prior authorization engine, configured to initiate requests to payers and/or adjudication computers for prior authorization. Additionally or alternatively, the prior authorization engine may predict prior authorization requirements and/or rejections such as based on configured prior authorization requirements maintained by the service provider computer 106 such as under the direction of a prescription benefit plan. The prior authorization may additionally or alternatively predict prior authorization requirements and/or rejections based on an analysis of historical claims and which claims have been previously rejected due to a need for prior authorization. The prior authorization engine is described in further detail herein.

The cash price data source 110 may comprise any computing device configured to provide cash pricing information to the service provider computer 106. For example, contractual pricing information pertaining to cash prices of prescription drugs at particular pharmacies may be maintained in the cash price data source 110, which may be maintained and/or accessed by the service provider computer 106. Patients may obtain prescriptions for the cash prices in some examples without the patient necessarily providing a cash discount card associated with a cash discount system, described in further detail below. However, according to some embodiments a patient may optionally utilize a cash discount card and/or cash discount system to purchase a prescription.

According to certain embodiments, the cash price data source 110 may optionally provide cash discount pricing information to the service provider computer 106. In some instances, a pharmacy works in agreement with a cash discount system to offer the cash price and/or discount on behalf of the cash discount system. Cash discount systems provide websites or mobile applications to track prescription drug prices and offer coupons or discounts on certain prescription medications. A patient may access the website or mobile application to check the cash price of a certain medication while taking into consideration any available discounts or coupons. The cash price is considered the amount paid without submitting a prescription claim to a payer such as a pharmacy benefits manager (PBM) or other health insurance plan. The patient may then compare the cash price to a price the patient would pay for the same prescription drug when submitting a prescription claim. In some instances, cash discount systems enable a patient to present a cash discount card and to obtain a medication at a lower cost than what would be obtainable by submitting a prescription claim to a PBM for the same medication. In this regard, according to certain embodiments, the cash price data source 110 may be a system or database of a cash discount system and/or a third party system configured to track pricing offered by the cash discount system.

According to certain embodiments, the cash price data source 110 may be maintained or operated by the pharmacy computer 104, such as in instances in which the pharmacy tracks historical data or historical pricing of cash transactions occurring at the pharmacy. The "cash price," as may be referred to herein, may be out of pocket cash prices to be paid by a patient. In certain examples, the cash price may be referred to as a cash price alternative, to emphasize the cash price is an alternative to a co-pay or out of pocket cost quoted by a prescription benefit plan and/or other insurance plan. A cash transaction that reflects a cash price may be a transaction in which a patient purchases or is to purchase a prescription drug without the claim being submitted to a prescription benefit plan, and/or in instances in which an initial claim is submitted, the claim maybe reversed in favor of the cash transaction. In scenarios in which cash transactions are utilized, the prescription may no longer be subject to prior authorization requirements and/or other restrictions enforced by a prescription benefit plan. Additionally, in a cash transaction, the manufacturer does not owe any contractual back-end rebates to the PBM, and can potentially give that money directly to patients in the form of assistance.

Regardless, without methods of a manufacturer and/or service provider setting or impacting a patient price, either through the benefit response and/or creating a cash price, for example, a patient that cannot afford a prescription has no ability to pick up and pay for a prescribed medication/ therapy. Example embodiments provided herein improve prescription adherence, and in some examples allow a patient to obtain a prescription more quickly than in other transactions (performed without the advantages of example embodiments) subject to prior authorization, by offering cheaper alternatives to a pharmacy's typical cash price, by way of the service provider computer's integration with a pharmaceutical manufacturer computer and defined contracts and agreements for the service provider computer to adjust pricing on behalf of a manufacturer. In this regard, the service provider computer 106 may store and access information related to contractual pricing associated with a manufacturer.

Referring now to FIG. 2, apparatus 200 is a computing device(s) configured for implementing pharmacy computer 104, service provider computer 106, adjudication computer 108, and/or cash price data source 110, according to example embodiments.

Apparatus 200 may at least partially or wholly embody or be embodied by any of the pharmacy computer 104, service provider computer 106, and/or adjudication computer 108. Apparatus 200 may therefore implement any of the pharmacy computer 104, service provider computer 106, and/or adjudication computer 108, in accordance with some example embodiments, or may be implemented as a distributed system that includes any of the pharmacy computer 104, service provider computer 106, adjudication computer 108, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the pharmacy computer 104 (such as when the pharmacy computer 104 is implemented as a service communicatively connected to a work station or other user device utilized by a pharmacist or other pharmacy employee), service provider computer 106, and/or adjudication computer 108. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the pharmacy computer 104, service provider computer 106, adjudication computer 108, cash price data source 110, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as pharmacy computer 104, service provider computer 106, adjudication computer 108, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry— in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a pharmacy computer 104, and/or adjudication computer 108. Memory 214 may further include reconciliation tables for tracking the healthcare transactions received from the pharmacy computer 104, and reconciling them with responses received from adjudication computer 108 and/or prior authorization requests or attempts to the PBM, which may not flow through the adjudication computer 108. The memory 214 may further comprise a database, such as cash price data source 110, comprising cash prices of particular medications. Still further, according to certain embodiments, the memory 214 may be modified as described herein, to reformat prescription claims and/or prescription transactions with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, content, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 is implemented as the pharmacy computer 104, the user interface 216 may, in some example embodiments, provide means for user entry of insurance information, details relating to the dispensing of a prescription, and/or the like. The user interface 216 may be further configured to display or provide messages relating to prior authorization, out of pocket costs of prescription medications, and/or the like, such as when apparatus 200 is implemented as a pharmacy computer 104. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of pharmacy computer 104, service provider computer 106, adjudication computer 108, cash price data source 110 and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., pharmacy computer 104, service provider computer 106, adjudication computer 108, cash price data source 110, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

Having now described an example apparatus for implementing example embodiments, FIG. 3 is a flowchart illustrating example operations of an apparatus 200, according to some example embodiments. The operations of FIG. 3 may be performed by apparatus 200, such as with the service provider computer 106, and/or the like.

As shown by operation 302, apparatus 200 may include means, such as processor 212, memory 214, communication interface 218, and/or the like, for receiving an indication of a prescription transaction comprising a patient identifier identifying a patient, a prescription identifier identifying a drug, and benefit information.

The prescription transaction may be received and/or routed from any of a prescriber computer, pharmacy computer, and/or adjudication computer.

For example, the prescription transaction may be received from the pharmacy computer 104, such as following entry by a pharmacist or other user of data relating to a prescription drug being obtained by a patient. In some examples, such as when an electronic prescription is submitted to a pharmacy computer from a healthcare provider computer, the patient may not yet be present at the pharmacy.

As another example, a prescription transaction may be submitted by a prescriber computer to an adjudication computer (e.g., via the service provider computer 106). In certain scenarios, the prescription transaction may be submitted by a physician for the purposes of prior authorization by a PBM, and may not necessarily include pharmacy information.

In certain examples, operation 302 may include receiving the prescription transaction from the adjudication computer 108, after it has been processed for prior authorization. Accordingly, the received prescription transaction may include a prescription transaction that was approved for benefits by a adjudicaton computer 108 and/or PBM.

In any event, the prescription transaction may further include or indicate benefit information such as but not limited to payer or plan identifier, group number, member identifier, and/or the like. The transaction may include or refer to, for example, one or more of the following information:

Payer ID/Routing Information
Transaction Payer Identifier(s) that designates a destination of the healthcare transaction (e.g., BIN Number, BIN Number and PCN, or BIN Number and Group ID)
Transaction Code
Patient Information
Name (e.g. Patient Last Name, Patient First Name, etc.)
Date of Birth of Patient
Age of Patient
Patient Gender Code
Patient Address (e.g. Street Address, Zip Code, etc.)
Patient Contact Information (e.g. patient telephone number, email address, etc.)
Patient Health Condition Information
Patient Identification Identifier (such as, but not limited to, patient social security number, a subset of the patient social security number, health insurance claim number (HICN), cardholder ID, etc.)
Insurance/Coverage and/or other Benefit Information Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy or other Healthcare Provider Information (e.g. store name, chain identifier, etc.)
Pharmacy or other Healthcare Provider ID (e.g. NPI code)
Claim Information
Drug, service, or product information (e.g. via National Drug Code (NDC) number)
Prescription/Service Reference Number
Date Prescription Written
Quantity Dispensed
Days' Supply
Diagnosis/Condition
Pricing information for the drug/service/product
Number of Refills Authorized
One or more Drug Utilization (DUR) Codes
Date of Service
Intermediary Authorization Field The prescription transaction may be received at the service provider computer 106 for further processing as described below.

As shown by operation 304, apparatus 200 may include means, such as processor 212, memory 214, communication interface 218, and/or the like, for classifying the prescription transaction as one classification of at least two classifications. A first classification may include an indication that a prescription benefit claim associated with the prescription transaction is at least one of denied or likely to be denied. For example, a prescription benefit claim may be denied or may be determined to likely be denied due to a requirement for prior authorization. A second classification may indicate the prescription transaction is not denied, is adjudicated, is approved, is unlikely to be denied, is likely to be adjudicated, and/or is likely to be approved. In certain embodiments, an approval may refer to an approval of prior authorization, and not necessarily an adjudicated and/or paid claim.

In certain embodiments and scenarios, such as when the prescription transaction received in operation 302 was rejected due to prior authorization, the service provider computer 106 may parse the transaction to determine the rejection for prior authorization, and determine the first classification.

According to certain example embodiments, and in scenarios such as when the prescription transaction received in operation 302 has not yet been processed by an adjudication computer 108, classification of the prescription transaction may be performed by a prior authorization engine configured to initiate a request to a payer for prior authorization, and/or to forward the prescription transaction for adjudication which in turn may invoke a prior authorization request. Additionally or alternatively, the prior authorization engine may make predictions regarding prior authorization requirements, and in certain embodiments, without forwarding the transaction to additional systems for further processing and/or adjudication.

According to certain example embodiments, classifying the prescription transaction may include transmitting a prescription claim associated with the prescription transaction, optionally formatted as a prescription claim and/or prescription benefit inquiry, to a payer computer, such as adjudication computer 108. Example embodiments may access a routing table or other data to determine a recipient adjudication computer 108 to which to transmit a prescription claim. In this regard, example embodiments may generate the prescription claim from information provided in the prescription transaction, or forward the prescription transaction as a claim to the adjudication computer 108. The prescription claim may be transmitted to the adjudication computer 108 in real-time or near real-time in response to receiving the prescription transaction from the pharmacy computer 104, thereby enabling the service provider computer 106 to provide a response to the pharmacy computer 104 regarding out-of-pocket costs or patient pay amount, as described in further detail below, in real-time or near real-time.

According to example embodiments and scenarios in which a prescription claim is routed for further processing, such as to a payer computer and/or adjudication computer 108, once received from the service provider computer 106, the payer computer and/or adjudication computer 108 may process the prescription claim and generate a benefit response message. For example, the adjudication computer 108 may adjudicate the prescription claim, such as according to plan policies. The adjudication computer 108 may further process the claim, and if approved and/or adjudicated, may include in a benefit response message the benefit amount, co-pay, and/or remaining balance owed for the prescription identified in the prescription claim. The benefit, co-pay, or remaining balance may vary depending on whether the deductible is met, depending on agreed upon pricing for the medication under the plan, and/or the like. Other rules and/or requirements may be processed and/or validated to determine the benefit. The benefit response message may be appended to or incorporated with the prescription transaction, such that if and when received by the service prover computer 106, the service provider computer 106 identifies the source of the response as associated with the originating prescription transaction received in operation 302. The processed, or adjudicated prescription claim, may be transmitted back to the service provider computer 106 as an adjudicated prescription claim. However, claims subject to prior authorization, and for which prior authorization requirements are not satisfied, may be rejected as described in further detail below.

In an event, apparatus 200 may include means, such as processor 212, memory 214, communication interface 218, and/or the like, for receiving a response from the adjudication computer 108. If the response is an adjudicated prescription claim, the second classification is determined, as approved and/or adjudicated, and processing may continue at operation 310, as described in further detail below. An adjudicated prescription claim may include an indication of approval and a co-pay amount, for example, and may not indicate any need for follow-up due to prior authorization requirements (either no prior authorization requirement exists, or the requirements are satisfied).

However, in some scenarios, submission of a response to a payer computer and/or adjudication computer 108 may result in a response that indicates a denial, reject code, rejection reason, indication of prior authorization requirement, and/or the like. In such examples, the first classification may be determined, and processing may continue at operation 316, as described in further detail below.

It will be appreciated that according to certain embodiments, a prescription claim may not necessarily need to be transmitted to an adjudication computer to determine the first or second class cation. The service provider computer 106 may alternatively utilize the prior authorization engine to assess the likelihood of adjudication, denial, and/or the like and classify the prescription transaction accordingly. For example, the service provider computer 106 may access and/or invoke a prior authorization engine to make predictions regarding prior authorization requirements, and which transactions are determined to satisfy or not satisfy any such requirements.

According to an example embodiments, the prior authorization engine may implement prior authorization requirements provided by and/or enforced by various prescription benefit plans. The prior authorization engine may then access prior prescription claims associated with the patient, and/or other data, to verify whether the prior authorization requirements defined by a benefit plan are satisfied for a transaction.

As another example, if a service provider computer 106 and/or prior authorization engine thereof does not have access to the exact prior authorization requirements may access historical records relating to prior prescription claims to predict whether a prescription claim could be rejected for a prior authorization requirement, for example. In this regard, the prior authorization engine may not necessarily be configured to implement prior authorization requirements for a prescription benefit plan, but make inferences based on prior claims rejected by a plan due to prior authorization requirements. For example, a classification may be predicted based on prior prescription claims for the same medication that has been previously rejected within the same prescription benefit plan.

In this regard, the service provider computer 106 and/or prior authorization engine thereof may predict whether a claim could be rejected for prior authorization requirements without communicating with the payer and/or adjudication computer 108. In some embodiments, the processor 212 may calculate a score, rating and/or other likelihood in determining a classification.

In any event, if the second classification is determined, indicating that a prescription claim associated with the prescription transaction is adjudicated, approved, likely to be adjudicated, and/or likely to be approved, at operation 310, apparatus 200 may include means, such as processor 212, memory 214, communication interface 218, and/or the like, for causing transmission of a prescription claim, such as to adjudication computer 108 if adjudication has not yet occurred, and/or a response to pharmacy computer 104, such as when an associated prescription claim has been adjudicated and/or to a prescriber computer 105, such as when the prescriber computer 105 submitted a request for prior authorization and/or a prescription inquiry to obtain pricing information (such as during a patient encounter). A response transmitted may include patient pay information and/or the like, and the patient may proceed to obtain their medication. In such scenarios as the second classification and/or operation 310, example embodiments may preclude and/or prevent determination of a credit amount and/or cash price alternative as discussed in further detail below as it relates to the first classification.

If the first classification is determined at operation 304, indicating denial, likely to be denied, unlikely to be adjudicated, and/or the like, various operations may be performed accordingly. According to certain example embodiments, the prescription transaction may optionally be prevented from being transmitted to the adjudication computer. In such scenarios, the service provider computer 106 may return the prescription transaction and/or inquiry, optionally including a reject reason, reject code or reject message, to request further information, and/or the like.

As shown by operation 316, apparatus 200 may include means, such as processor 212, memory 214, communication interface 218, and/or the like, for determining a cash price of the drug available, such as may be available via a cash system, directly from the pharmacy, and/or the like. The cash price may therefore reflect an amount that a patient may pay for the drug without the application of a prescription benefit plan. For example, example embodiments may access or receive the cash price of the drug from a pharmacy computer 104. The drug pricing for cash transactions occurring at the pharmacy may be set, tracked and/or updated by the service provider computer 106 on an as-needed basis, and optionally maintained in a pricing database such as cash price data source 110 and/or memory 214, for example. In this regard, the service provider computer 106 may set cash prices directly based on reimbursement contracts with pharmacies, as funded by a manufacturer with an automatic adjustment of the claim, or through another vehicle like a cash discount system, (e.g., cash card) where the card sets the financial claim itself. According to example embodiments provided herein, the cash price may be automatically obtained and inserted into a prescription transaction (rather than forwarding the prescription claim to a PBM), if it is determined a prior authorization attempt was denied.

According to certain example embodiments, in instances in which cash discount systems are utilized, the service provider computer 106 may optionally store and utilize historical cash prices from prior prescription transactions that were forwarded from the pharmacy computer 104 to the service provider computer 106 for adjudication. In this regard, the service provider computer 106 may function as or comprise an adjudication switch configured for receiving prescription transactions from the pharmacy computer 104 and routing the transactions accordingly. As such, some transactions may be forwarded to an adjudication computer 108 associated with a cash discount system, and/or some transactions may be forwarded to the associated cash discount system. Transactions forwarded to a cash discount system may be stored, and a corresponding response received from the cash discount system indicating the cash prices. Example embodiments may return the cash price to the pharmacy computer 104 and/or store the cash price in a database and/or memory 214. As such, the service provider computer 106 may maintain the cash prices and utilize historical cash prices to predict or determine the cash price of a particular prescription drug. In this regard, in certain embodiments, the cash price may be appended to the prescription transaction information, such as by the pharmacy computer 104, and received by the service provider computer 106 as described with respect to operation 302.

As another example, the cash price may optionally be obtained by the service provider computer 106 by systematically accessing a website, application programming interface, or other service of a cash discount system. In certain example embodiments, the memory 214 may be configured with computer program code configured as a web bot or script to systematically access a mobile application or website of the cash discount system and obtain cash prices. For example, the cash price could be obtained in real-time or near real-time responsive to receipt of the prescription transaction in operation 302. As another example, a web bot or script may access the website or mobile application of the cash discount system independent of a particular prescription transaction, and store the cash prices offered by particular pharmacies for certain medication in the cash price data source 110, or other memory, such as memory 214.

In any event, example embodiments may receive the cash price in real-time or near real-time responsive to the receipt of the prescription transaction, enabling a real-time or near real-time response to be provided to the pharmacy computer 104 as described in further detail below.

As used throughout, the terms real-time and near real-time indicate a seemingly instant response time at the pharmacy computer 104, such that a patient obtaining a prescription may obtain pricing information and the patient pay amount (as described in further detail below and with respect to FIG. 3), as the pharmacist or other employee interacts with a user interface of the pharmacy computer 104 or a user interface in communication with the pharmacy computer 104. As yet another example, the response may be provided to a pharmacy computer 104 and/or the like in real-time responsive to a submission of an electronic prescription being sent from a healthcare provider computer to the pharmacy computer 104, which the pharmacy computer 104 further processes as described herein. It will be appreciated that despite the reference to real-time or near real-time, certain delays based on computer processing time may be encountered.

Moreover, it will be appreciated that the cash price determined with respect to operation 316 may be referred to as a predicted cash price, or estimated cash price, due to certain embodiments utilizing historical data and/or other means to predict or estimate the cash price. As another example, the service provider computer 106 may set the cash price of a prescription drug without accessing prior claims, such as based on a ratio of a published benchmark As shown by operation 320, apparatus 200 may include means, such as processor 212, memory 214, and/or the like, to determine a credit amount to be applied to the cash price. The credit amount may be determined in a variety of ways. For example, the credit amount may be a predetermined percentage discount, such as 25%. In some embodiments, prescription drugs may be classified into formulary tiers, and different tiers may have different associated percentages on which credit amounts are based. Based on allotments provided by manufacturers, the credit amount could be capped. As yet another example, the credit amount may be determined at least partially on what the patient pay amount for the prescription drug would be predicted to be under a benefit plan if an associated prescription claim were approved, even if it was not approved in such a circumstance such as one requiring prior authorization. The credit amount may represent an amount to be paid by, or made up by a party, such as the pharmaceutical manufacturer, or other third party provider.

According to certain example embodiments, the service provider computer 106, such as with processor 212, may be configured to generate a price sensitivity model for a particular prescription drug(s). For example, a percentage or ratio of abandonment (e.g., when the patient fails to purchase their prescription, or reverses an insurance claim to pay a cash price), for transactions reflecting a particular co-pay or patient pay amount or range thereof. Example embodiments may therefore utilize regression analysis to determine a remaining patient pay amount to use as a target, in an effort to increase and/or improve, the number of completed transactions relative to completion of prior transactions. In this regard, the price sensitivity model may be utilized to determine a remaining patient pay amount, and therefore, the credit amount, and reduce the number of abandoned or reversed prescription transactions. For example, processor 212 may determine the remaining patient pay amount, and therefore, the credit amount, to attempt to reach a goal of 98% (or any other goal) completed prescription transactions, based on the price sensitivity model and regression analysis applied thereto.

A credit amount may be further determined such that the cash price available at a pharmacy, with the credit amount applied, may be lower than a cash discount price obtainable via a cash discount system.

As another example, example embodiments may determine or estimate a cash price, including in instances in which a pharmacy is not indicated in a transaction (such as when the prescriber computer 105 transmits a prescription transaction for prior authorization) based on one or more benchmarks such as but not limited to a Drug Wholesale Acquisition Cost (WAC), Average Wholesale Price (AWP), National Average Drug Acquisition Cost (NADAC), and/or the like. In this regard, the service provider computer 106 may set the cash price as a discount based on a benchmark and the pharmacy earns the same as under a contracted dispense fee.

It will be appreciated that many other rules, formulas, algorithms, and/or combinations thereof, may be contemplated for determining the credit amount and/or remaining patient pay amount.

After determining a credit amount, a remaining patient pay amount may be calculated as the cash price, estimated cash price, or cash price alternative, minus the determined credit amount. In this regard, certain example embodiments may be implemented such that the remaining patient pay amount is competitive with a patient pay amount that could otherwise be achieved with an approved and/or authorized prescription claim through a benefit plan, even though an associated prescription claim is rejected and/or likely to be rejected such as based on a preauthorization requirement.

As shown by operation 326, apparatus 200 may include means, such as processor 212, memory 214, communication interface 218, and/or the like, for reformatting the prescription transaction to a format that indicates a cash transaction and the credit amount. In this regard, the prescription transaction may be rerouted and/or redirected. The prescription claim initially intended for an adjudication computer 108 associated with a prescription benefit plan is intercepted, and optionally prevented from being transmitted to the adjudication computer 108 (or prevented from being resubmitted, if the prescription transaction was already processed by the adjudication computer 108 and rejected, for example). If however a transaction that was replace with a cash transaction according to example embodiments, was transmitted to an adjudication computer 108, such a transaction may be reversed by the service provider computer 106 transmitting a reversal.

In some embodiments the reformatted prescription transaction that indicates the cash transaction may be readable by the recipient such as a pharmacy computer and/or prescriber computer, and may further include the remaining patient pay amount, and an indication and/or message that the credit amount is applicable to a cash price and/or cash transaction, rather than a prescription claim under a prescription benefit plan. The reformatted prescription transaction may exclude the prescription benefit information included in an originally received prescription transaction, as the proposed pricing can be achieved via a cash transaction and not the prescription benefit plan. The cash transaction is therefore not subject to the prior authorization requirements enforced by the payer and/or adjudicator, and may cause a reduction in a number of follow-up transactions and/or data communication otherwise required to satisfy prior authorization requirements.

As shown by operation 332, apparatus 200 may include means, such as processor 212, memory 214, communication interface 218, and/or the like, to transmit the reformatted prescription transaction. In certain embodiments, the reformatted prescription transaction may be transmitted to a pharmacy computer 104. The information in the reformatted prescription claim can therefore be transmitted to the pharmacy computer 104 for provision via a user interface, such that the remaining patient pay amount can be communicated to the patient. Additionally or alternatively, the reformatted prescription transaction may be transmitted to prescriber computer 105, such as in instances in which the prescriber computer 105 submitted a request for prior authorization, and/or the prescriber computer 105 attempts to obtain pricing information of the prescription drug in real-time or near real-time, such as during a patient encounter, for example.

Accordingly, even if a prescription claim is rejected, such as for a prior authorization requirement, the patient may choose to purchase the prescription with cash. In this regard, manufacturers may be more willing to offer financial assistance in scenarios in which a prescription claim was denied based on prior authorization requirements, such that patients are encouraged to adhere to the prescription and purchase the medication that may otherwise be unaffordable. Accordingly, the service provider computer 106 creates value for the manufacturer by leveraging the information indicative of a prior authorization denial, as it functions as a switch, processor, and router of prior authorization requests and related claims, and can detect prior authorization rejections prior to returning a response to a pharmacy computer 104. In this regard, example embodiments intercept such prior authorization rejections, apply an identified cash price, reformat the transaction as a cash transaction, and route the reformatted transaction to the pharmacy computer and/or prescriber computer. It will be appreciated that according to certain embodiments, and in certain scenarios, a prescription claim that would otherwise be rejected due to prior authorization requirements, may be intercepted prior to any communication with a potential recipient (such as a pharmacy computer or prescriber computer), and reformatted as the cash transaction accordingly). The reformatted prescription transaction may further include a message or associated code indicating the prescription transaction was changed to a cash transaction rather than submitted as prescription claim to the PBM.

As set forth above, example embodiments partition prescription transaction costs by determining a credit amount based on an alternative cash price of a prescription drug. In certain example embodiments, as shown in operation 334, apparatus 200 may include means, such as processor 212, memory 214, communication interface 218, and/or the like, to transmit the credit amount to a third party computer. For example, the credit amount may be transmitted to a computer associated with the pharmaceutical manufacturer, such as for record keeping, and/or the like.

Example embodiments provided herein therefore provide a technical solution to several technical problems. In the realm of denied prescription claims, such as to satisfy prior authorization requirements, rejected prescription claims are logged, tracked, and routed amongst computers and/or networks, including the pharmacy computer, prescriber computer (associated with a physician and/or the like), an adjudication computer, and a service provider computer. In some cases, information must be corrected and/or appended to a prescription traction in order for prior authorization to be granted. This may include collecting and routing information provided by physicians, prescribers, other prescription benefit plans, such as a prior prescription benefit plan of the patient, and/or the like. The tracking and routing of such transactions expends additional processing, memory, and network resources.

However, according to the technical solutions provided by example embodiments, the service provider computer 106 may determine a prescription claim is denied or likely be denied, and determine, in real-time or near real-time, a credit amount that may result in the patient purchasing the prescription at a cash price rather than facilitating the resubmission and additional processing of claims that are initially denied. The additional processing, memory, and network resources otherwise expended on the tracking, routing, and updates to such transactions may therefore be reduced according to the example embodiments provided herein.

Example embodiments are therefore integrated into a practical application of systematically partitioning prescription transactions by determining a credit amount to be applied to a prescription traction based on an alternative cash price. Additionally, example embodiments are integrated into a practical application of improving prescription adherence by providing a real-time cash price alternative, with a credit amount applied, responsive to determining a claim is denied or likely to be denied.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the at least one processor, cause the apparatus to at least:
   receive, by a service provider computer, an indication of a prescription transaction comprising a patient identifier identifying a patient, a prescription identifier identifying a drug, and benefit information associated with a first adjudication computer to which the prescription transaction is directed;
   in real-time or near real-time relative to receiving the indication of the prescription transaction:
      determine, by the service provider computer, that the prescription transaction is denied based on a response from a first adjudication computer or is predicted to likely be denied by invoking a prior authorization engine configured to access stored claims previously rejected based on a requirement for prior authorization;
      in response to determining the prescription transaction is denied or predicted to likely be denied, execute a script configured to access a cash discount system to determine a cash price of the drug;
      further in response to determining the prescription transaction is denied or predicted to likely be denied, determine, by the service provider computer, a credit amount to be applied to the cash price;
      further in response to determining the prescription transaction is denied or predicted to likely be denied, and prior to adjudication of a claim associated with the prescription transaction, reformat the prescription transaction to a format associated with a second adjudication computer, different that the first adjudication computer, wherein the reformatted prescription transaction indicates a cash transaction and the credit amount, such that the reformatted prescription transaction is not subject to preauthorization requirements; and
      redirect the prescription transaction and cause transmission of the reformatted prescription transaction including the indication of the cash transaction and the credit amount to at least one of a prescriber computer from which the prescription transaction was received, a pharmacy computer from which the prescription transaction was received, or the second adjudication computer.

2. The apparatus according to claim 1, wherein the cash price of the drug is determined based on contractual pricing associated with a manufacturer.

3. The apparatus of claim 1, wherein the at least one memory and the computer program code are configured to, with the processor, cause the apparatus to at least:
   transmit the credit amount to a third party computer.

4. A method comprising:
   receiving an indication of a prescription transaction comprising a patient identifier identifying a patient, a prescription identifier identifying a drug, and benefit information associated with a first adjudication computer to which the prescription transaction is directed;
   in real-time or near real-time relative to receiving the indication of the prescription transaction:
      determining the prescription transaction is denied or predicted to likely be denied based on a requirement for prior authorization;
      in response to determining the prescription transaction is denied or predicted to likely be denied based on the requirement for the prior authorization, determining a cash price of the drug;
      further in response to determining the prescription transaction is denied or predicted to likely be denied based on the requirement for the prior authorization, determining a credit amount to be applied to the cash price;
      reformatting the prescription transaction to a format that indicates a cash transaction and the credit amount; and
      redirecting the prescription transaction and causing transmission of the reformatted prescription transaction including the indication of the cash transaction and the credit amount to a second adjudication computer, different than the first adjudication computer.

5. The method according to claim 4, wherein the first classification comprises an indication that a prescription benefit claim associated with the prescription transaction is at least one of denied or likely to be denied.

6. The method according to claim 4, wherein the cash price of the drug is determined based on contractual pricing associated with a manufacturer.

7. A computer program product comprising at least one non-transitory computer-readable storage medium having computer-executable program code instructions stored therein, the computer-executable program code instructions comprising program code instructions to:
- receive an indication of a prescription transaction comprising a patient identifier identifying a patient, a prescription identifier identifying a drug, and benefit information associated with a first adjudication computer to which the prescription transaction is directed;
- in real-time or near real-time relative to receiving the indication of the prescription transaction:
  - determine the prescription transaction is denied or determined to likely be denied based on a requirement for prior authorization;
  - in response to determining the prescription transaction is denied or predicted to likely be denied based on the requirement for the prior authorization, determine a cash price of the drug;
  - further in response to determining the prescription transaction is denied or predicted to likely be denied based on the requirement for the prior authorization, determine a credit amount to be applied to the cash price;
  - reformat the prescription transaction to a format that indicates a cash transaction and the credit amount; and
  - redirect the prescription transaction and cause transmission of the reformatted prescription transaction including the indication of the cash transaction and the credit amount to a second adjudication computer, different than the first adjudication computer.

8. The computer program product according to claim 7, wherein the cash price of the drug is determined based on contractual pricing associated with a manufacturer.

* * * * *